US009821263B2

(12) United States Patent
Hering et al.

(10) Patent No.: US 9,821,263 B2
(45) Date of Patent: Nov. 21, 2017

(54) ADVANCED LAMINAR FLOW WATER CONDENSATION TECHNOLOGY FOR ULTRAFINE PARTICLES

(71) Applicant: Aerosol Dynamics Inc., Berkeley, CA (US)

(72) Inventors: Susanne V. Hering, Berkeley, CA (US); Gregory S. Lewis, Berkeley, CA (US); Steven R. Spielman, Oakland, CA (US)

(73) Assignee: AEROSOL DYNAMICS INC., Berkeley, CA (US)

( * ) Notice: Subject to any disclaimer, the term of this patent is extended or adjusted under 35 U.S.C. 154(b) by 182 days.

(21) Appl. No.: 14/318,126

(22) Filed: Jun. 27, 2014

(65) Prior Publication Data

US 2015/0075372 A1 Mar. 19, 2015

Related U.S. Application Data

(62) Division of application No. 13/218,393, filed on Aug. 25, 2011, now Pat. No. 8,801,838.
(Continued)

(51) Int. Cl.
*B01D 53/00* (2006.01)
*B01D 5/00* (2006.01)
(Continued)

(52) U.S. Cl.
CPC ......... *B01D 53/002* (2013.01); *B01D 5/0009* (2013.01); *G01N 15/065* (2013.01);
(Continued)

(58) Field of Classification Search
CPC ................ B01D 53/002; B01D 5/0009; B01D 2257/504; B01D 53/1475; G01N 15/065;
(Continued)

(56) References Cited

U.S. PATENT DOCUMENTS 3,825,790 A * 7/1974 Bacal ........................ G21K 1/14 313/362.1
4,293,217 A 10/1981 Bird, Jr. et al.
(Continued)

FOREIGN PATENT DOCUMENTS

EP 0462413 A2 12/1991
EP 2208983 A2 7/2010
(Continued)

OTHER PUBLICATIONS

Amendment dated Jan. 19, 2016, in Chinese Patent Appl. No. 201180052428.5 filed Aug. 26, 2011, with English translation of the amended claims.
(Continued)

*Primary Examiner* — Dung H Bui
(74) *Attorney, Agent, or Firm* — Vierra Magen Marcus LLP

(57) ABSTRACT

This technology relates to the enlargement by water condensation in a laminar flow of airborne particles with diameters of the order of a few nanometers to hundreds of nanometers to form droplets with diameters of the order of several micrometers. The technology presents several advanced designs, including the use of double-stage condensers. It has application to measuring the number concentration of particles suspended in air or other gas, to collecting these particles, or to focusing these particles.

20 Claims, 19 Drawing Sheets

Related U.S. Application Data

(60) Provisional application No. 61/402,348, filed on Aug. 27, 2010.

(51) Int. Cl.
*G01N 15/06* (2006.01)
*G01M 15/10* (2006.01)
*B01D 53/14* (2006.01)
*H04L 12/863* (2013.01)
*G01N 15/00* (2006.01)
*G01N 15/14* (2006.01)

(52) U.S. Cl.
CPC .... *B01D 53/1475* (2013.01); *B01D 2257/504* (2013.01); *G01M 15/102* (2013.01); *G01N 2015/0038* (2013.01); *G01N 2015/1481* (2013.01); *H04L 47/50* (2013.01); *Y02T 10/47* (2013.01)

(58) Field of Classification Search
CPC .. G01N 2015/1481; G01N 2015/0038; G01M 15/102; Y02T 10/47; H04L 47/50
See application file for complete search history.

(56) References Cited

U.S. PATENT DOCUMENTS

| | | | | |
|---|---|---|---|---|
| 4,790,650 | A | 12/1988 | Keady | |
| 5,675,405 | A | 10/1997 | Schildmeyer et al. | |
| 6,712,881 | B2 | 3/2004 | Hering et al. | |
| 7,298,486 | B2 * | 11/2007 | Wang ................. | G01N 15/0266 324/71.4 |
| 7,736,421 | B2 | 6/2010 | Hering et al. | |
| 2004/0020362 | A1 | 2/2004 | Hering et al. | |
| 2006/0126056 | A1 | 6/2006 | Roberts et al. | |
| 2008/0083274 | A1 | 4/2008 | Hering et al. | |
| 2012/0048112 | A1 | 3/2012 | Hering et al. | |

FOREIGN PATENT DOCUMENTS

| | | | |
|---|---|---|---|
| WO | 03065005 | A2 | 8/2003 |
| WO | 2008058182 | A2 | 5/2008 |

OTHER PUBLICATIONS

Office Action dated May 6, 2015, in Chinese Patent Appl. No. 201180052428.5 filed Aug. 26, 2011.

Hering, Susanne V., et al., "A Method for Particle Size Amplification by Water Condensation in a Laminar, Thermally Diffusive Flow," Aerosol Science and Technology, 39: 428-436, Mar. 2005, 9 pages.

Hering, Susanne V., et al., "A Laminar-Flow, Water-Based Condensation Particle Counter (WCPC)," Aerosol Science and Technology, 39: 659-672, Apr. 2005, 14 pages.

Stolzenburg, Mark R., et al., "An Ultrafine Aerosol Condensation Nucleus Counter," Aerosol Science and Technology, 14: 48-65, Jan. 1991, 19 pages.

Invitation to Pay Additional Fees and Communication Relating to the Results of the Partial International Search dated Nov. 4, 2011, in International Patent Application No. PCT/US2011/049391 filed Aug. 26, 2011.

Seager, Spencer L., et al., "Temperature Dependence of Gas and Vapor Diffusion Coeeficients," Journal of Chemical & Engineering Data, vol. 8, No. 2, Apr. 1, 1963, pp. 168-169.

International Search Report dated Jan. 18, 2012, International Application No. PCT/US2011/049391.

Leaitch, et al., "The Diffusion Tube: A Cloud Condensation Nucleus Counter for Use Below 0.3% Supersaturation" J. Aerosol Sci.. vol. 13, No. 4, pp. 297-319, Nov. 1981.

Restriction dated Apr. 9, 2013, in U.S. Appl. No. 13/218,393, filed Aug. 25, 2011.

Amendment dated Apr. 9, 2013, in U.S. Appl. No. 13/218,393, filed Aug. 25, 2011.

Office Action dated Apr. 9, 2013, in U.S. Appl. No. 13/218,393, filed Aug. 25, 2011.

Amendment dated Jan. 23, 2014, in U.S. Appl. No. 13/218,393, filed Aug. 25, 2011.

Notice of Allowance dated Mar. 28, 2014, in U.S. Appl. No. 13/218,393, filed Aug. 25, 2011.

Amendment dated Jan. 19, 2015, in Chinese Patent Appl. No. 201180052428.5 filed Aug. 26, 2011.

Office Action dated Jun. 2, 2015, in Japanese Patent Appl. No. 2013-526180 filed Aug. 26, 2011.

Amendment dated Sep. 28, 2015, in Japanese Patent Appl. No. 2013-526180 filed Aug. 26, 2011.

Amendment dated Jul. 21, 2015, in Chinese Patent Appl. No. 201180052428.5 filed Aug. 26, 2011.

Office Action dated Nov. 4, 2015, in Chinese Patent Appl. No. 201180052428.5 filed Aug. 26, 2011.

Office Action dated Sep. 9, 2014, in Chinese Patent Appl. No. 201180052428.5 filed Aug. 26, 2011.

Office Action dated May 5, 2016, in Chinese Patent Appl. No. 201180052428.5 filed Aug. 26, 2011.

Amendment filed Sep. 18, 2016, in Chinese Patent Appl. No. 201180052428.5 filed Aug. 26, 2011.

* cited by examiner

Diffusive Mixing with initiator - equilibrator

Diffusive Mixing with initiator - equilibrator

Parallel Plate with initiator – equilibrator

Parallel Plate with initiator – equilibrator

Initiator-Evaporator saturation profiles

Initiator-Evaporator saturation profiles evolution of droplet diameter

Initiator – Stabilizer

ADVANCED LAMINAR FLOW WATER CONDENSATION TECHNOLOGY FOR ULTRAFINE PARTICLES

CROSS REFERENCE TO RELATED APPLICATION

This application is a divisional of U.S. patent application Ser. No. 13/218,393, entitled “Advanced Laminar Flow Water Condensation Technology for Ultrafine Particles”, filed Aug. 25, 2011, which application claims the benefit of U.S. Provisional Application Ser. No. 61/402,348, entitled “A Kinetically Limited Growth Cell for Concentration Independent Water Condensation on Airborne Particles”, filed Aug. 27, 2010.

This invention was made with government support under the following Grant Nos: U.S. Dept. of Energy Grant #DE-SC0004643; and National Institutes of Health Grant #ES014997. The government has certain rights in the invention.

BACKGROUND

Field of the Technology

The present technology is directed to the measurement of the number concentration of airborne particles, to the focusing particles while airborne and to the collection of airborne particles through growth by water condensation. Specifically, it relates to particles in the size range from a few nanometers to a few micrometers in diameter.

Description of Related Art

Most airborne particles are difficult to detect directly because they have diameters smaller than the wavelength of visible light. Often condensational growth is used to enlarge these particles to a size that can be detected optically, thereby providing a means to readily measure airborne particle number concentrations. Condensational enlargement is also used to enable the aerodynamic focusing or collection of particles for chemical or exposure analyses.

Ultrafine particles, with diameters in the nanometer to hundreds of nanometers, are not easily enlarged by condensation. In almost all cases these ultrafine particles must be in an environment of vapor supersaturation before they will start to grow by condensation. Vapor supersaturation means that the concentration is larger than the vapor equilibrium concentration over a flat surface. This enhanced amount of vapor is needed to overcome the particle surface energy associated with its curvature and surface tension.

Hering and Stolzenburg introduced a means to create a supersaturation of water vapor in a laminar flow (U.S. Pat. No. 6,712,881, Hering, S V; Stolzenburg, M R, “A method for particle size amplification by water condensation in a laminar, thermally diffusive flow”, *Aerosol Science and Technology* 39: 428-436, 2005). Previously, laminar flow condensation methods had used a slowly diffusing species such as butanol as the condensing fluid. The method of Hering and Stolzenburg explicitly accounts for the high molecular diffusivity of water vapor, and achieves growth by water condensation in a laminar flow using a single-stage, warm, wet-walled condenser.

A second laminar flow method for producing small particle growth by water condensation is the “diffusive mixing” approach described by Hering and Lewis (U.S. Pat. No. 7,736,421). This method surrounds the aerosol flow with a warmer, saturated sheath flow in a laminar manner. Once joined, heat and water vapor are exchanged between the two flows by diffusion. Water vapor diffuses into the colder aerosol flow at a slightly higher rate than it is warmed by the surrounding flow, creating a region of water vapor supersaturation within the aerosol flow.

SUMMARY

Multiple embodiments of technology for laminar flow water condensation systems are disclosed. In one aspect, the use of narrower flow dimensions minimizes the effects of the sampled particle number concentration on the system performance. In a second aspect, a double stage condenser is presented which lowers the temperature and water vapor content of the exiting flow. This second aspect may implemented in combination with the narrower dimensions of the first aspect. In a third aspect, a different type of double-stage condenser design is presented for specialized applications requiring more uniform yet limited droplet growth, such as when droplets are used as absorbers for material in the vapor phase. In a fourth aspect a design is presented to allow for longer residence times for particle activation and growth at low supersaturation, as required for the testing of diesel exhaust particulate matter. Each of these embodiments have been identified through numerical modeling tools developed to describe the laminar flow condensation system. These embodiments are applicable to a variety of geometries including both tubular and parallel plate configurations.

BRIEF DESCRIPTION OF THE DRAWINGS

FIG. 12*a* shows a 9.5 mm diameter tube, FIG. 12*b* shows a 6.4 mm diameter tube and FIG. 12*c* shows a 4.6 mm diameter tube.

DETAILED DESCRIPTION

Laminar flow water condensation technology is used to condense water onto ultrafine particles suspended in air or other gaseous medium, and to grow them by condensation to form droplets of a few micrometers in diameter. Particles of this size can then be analyzed using a variety of techniques.

Figure 1A:
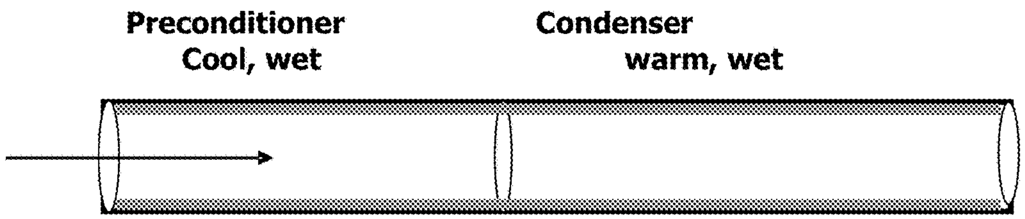
FIGS. 1*a* and 1*b* illustrate the laminar flow condensation methods of the prior art.

A laminar flow water condensation system as described in U.S. Pat. No. 6,712,881, is referred to herein as "differentially diffusive". Generally it consists of a preconditioner followed by a condenser, both of which have wetted cylindrical walls, as illustrated in FIG. 1*a*. These may be constructed from a tube through which the airflow passes in a mostly laminar manner. Alternatively, the walls may be parallel plates. In either geometry the temperatures of the walls are controlled so that the walls of the condenser are warmer than the walls of the preconditioner. In accordance with known teachings, a thermoelectric device may be used to regulate the temperature of the preconditioner walls, and a heater used to regulate the temperature of the condenser walls. Alternatively one may use thermoelectric device employed as a heat pump to cool the preconditioner and warm the condenser. As the cooler laminar flow passes from the cooler precondtioner through the warmwet-walled condenser, both water vapor and heat diffuse into the flow from the walls. Due to its higher diffusivity, the water transport is more rapid, creating a region of vapor supersaturation with its maximum along the centerline.

The first commercially used embodiment of the differentially diffusive method of U.S. Pat. No. 6,712,881 used a single tube 230 mm in length, with an inner diameter of 9.5 mm, with an air flow rate of 1 L/min (Hering, S V; Stolzenburg, M R; Quant, F R; Oberreit D R., Keady, P B., A laminar-flow, water-based condensation particle counter (WCPC), *Aerosol Science and Technology,* 39: 659-672, 2005)). The entire tube was lined with a wetted wick. The first half was maintained at a temperature of about 20° C. and served as the preconditioner. The second half was heated to 60° C., and served as the condenser.

Figure 1B:
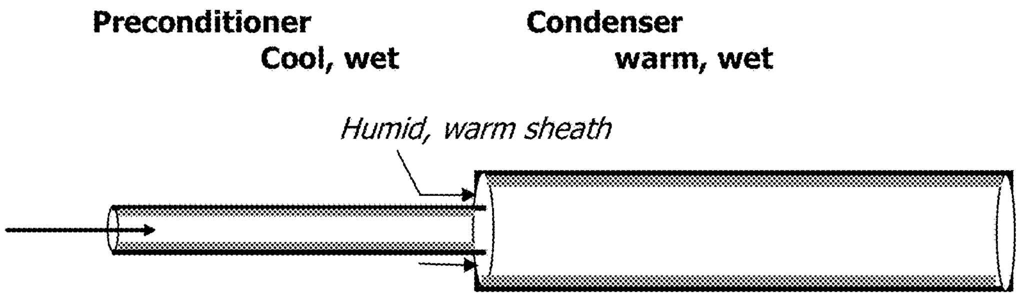

The laminar flow water condensation method described by U.S. Pat. No. 7,736,421 is referred to here as "diffusive mixing". As shown in FIG. 1*b* this approach may be implemented with a preconditioner followed by a condenser, wherein the sample air flow exiting the preconditioner is surrounded by a sheath of warm, saturated or partially supersaturated air before it enters the condenser. The walls of the condenser are wet, and warmed to the match the dew point of the sheath flow. As the two flows are joined in a laminar manner, the water vapor and heat diffuse from the sheath flow into the cooler particle flow, creating a region of water vapor supersaturation within the particle flow.

In a unique aspect of the present technology the condenser design is advanced. The condenser is where the water vapor supersaturation is created to initiate condensational growth on particles in the submicrometer to nanometer size range, and it is where these particles are subsequently grown through condensation to form droplets several micrometers in diameter. The creation of a region of vapor supersaturation is inherently an nonequlibrium process that relies on the relative rates of heat and water vapor transport.

Figure 2A:
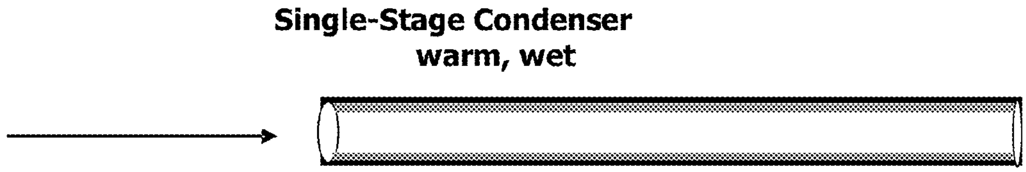
FIG. 2*a* illustrates a first embodiment of a condenser in accordance with the present technology.
Figure 3A:
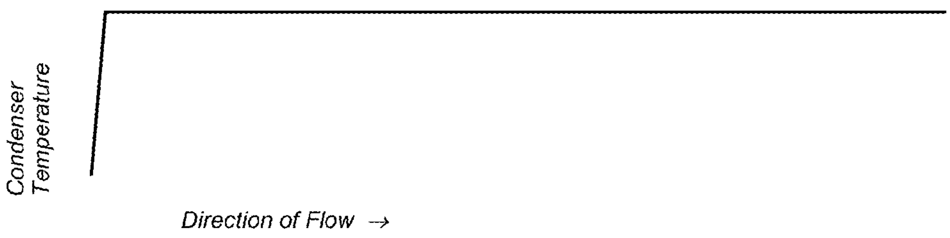
FIG. 3*a* is a plot of a temperature profile for the condenser designs of FIG. 2*a*.

The first aspect of the technology disclosed herein shows that by using narrower dimensions in the condenser, either smaller diameter tubes or more closely spaced parallel plates, the performance can be improved over a wide range of particle concentrations. Specifically, reducing the tube diameter of the first system (FIG. 2*a*) from 9.5 mm to 4.6 mm the smallest size of particles that is activated to growth through condensation is less affected by the number concentration of the particle sampled. Similarly, use of parallel plates with a gap of 3 mm provides more uniform performance over a wide range of concentrations. It has been found that a tube diameter in the range of 2 mm to 5 mm inclusive and a parallel plate spacing in the range of 2 mm to 5 mm inclusive work well in the present technology This narrower condenser is illustrated in FIG. 2*a*. It can be used with either the differentially diffusive approach of FIG. 1*a* or diffusive mixing approach of FIG. 1*b*. This first aspect uses the same temperature profiles in the condenser as disclosed by the prior patents. This temperature profile is illustrated in FIG. 3*a* which is a graph of the temperature of the condenser along the length of the condenser in the direction of the flow through the condenser. Apart from a short ramp at the entrance to cover the transition from the preconditioner, the condenser walls have a uniform temperature which is warmer than that of the entering flow.

Figure 2B:
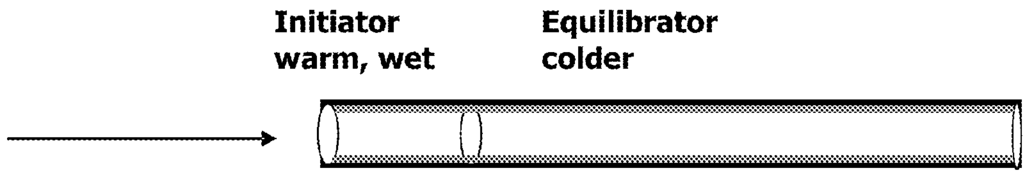
FIG. 2*b* illustrates a second embodiment of a condenser in accordance with the present technology.

The second aspect of the technology presented replaces the original single-temperature zone condenser with a two-stage condenser consisting of a short warm "initiator" section followed by a longer colder "equilibrator" section, with wetted walls throughout. This is illustrated in FIG. 2*b*. The combined length required for the initiator and equilibrator is approximately the same as that required for the original single-temperature zone condenser or about 12 cm for a flow of 1 L/min.

Figure 3B:
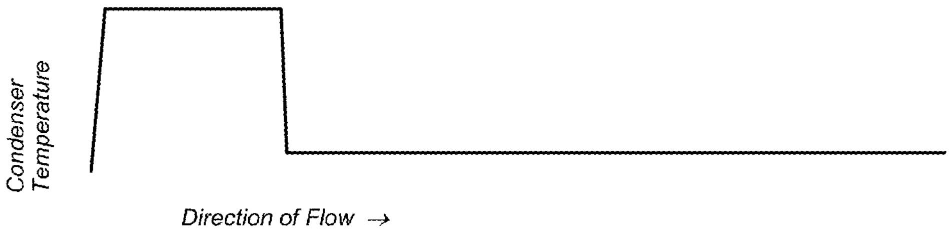
FIG. 3*b* is a plot of a temperature profile for the condenser designs of FIG. 2*b*.

This technology is referred to as the "initiator-equilibrator" condenser. Its temperature profile is illustrated in FIG. 3*b*, and shows a quick rise from the temperature of the preconditioner to a relatively short warm section, followed by a longer cooler section. As will be shown the performance is similar to that of the original single-temperature zone condenser, with the advantage that it is possible to reduce the temperature and dew point of the exiting flow.

Figure 2C:
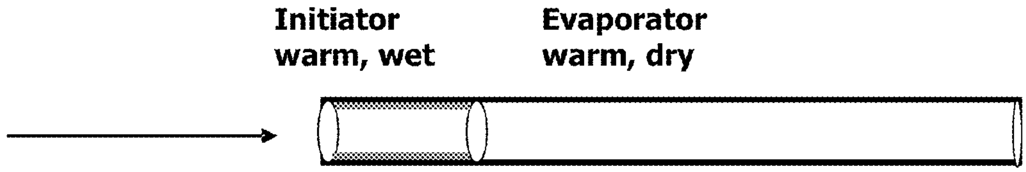
FIG. 2*c* illustrates a third embodiment of a condenser in accordance with the present technology.
Figure 3C:
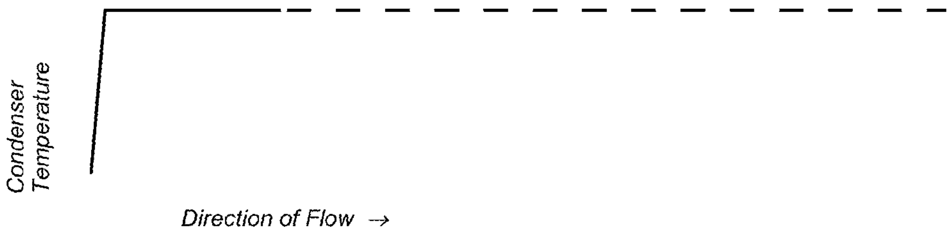
FIG. 3*c* is a plot of a temperature profile for the condenser designs of FIG. 2*c*.

The third aspect of the technology replaces the relatively cold, wet walled equilibrator described above with a warm, dry-walled "evaporator". This technology is illustrated in FIG. 2*c*. The wall temperature of the evaporator may be the same, or slightly higher than that of the initiator. In one embodiment, the temperature of the initiator is about 50° C. and that of the evaporator is about 50° C. The initiator has a wick or other means to maintain wetted walls, however the evaporator has no wick. Because the temperature of the evaporator walls is as high, or higher than the dew point of the flow exiting the initiator, these walls stay dry. The temperature profile for the initiator-evaporator condenser is shown in FIG. 3*c*, where a dotted line indicates that the evaporator walls are dry. This approach limits the maximum droplet size, and can be configured to re-evaporate the droplets formed. This aspect of the technology has application where short interaction between the droplet and material in the surrounding vapor is desired.

Figure 2D:
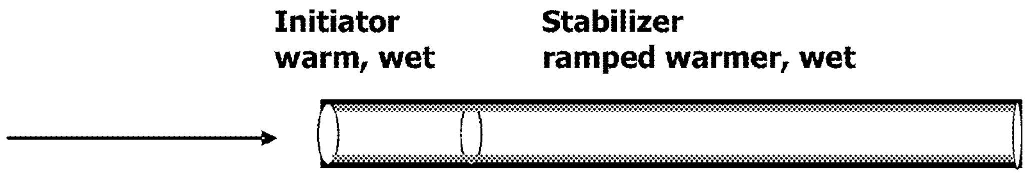
FIG. 2*d* illustrates a fourth embodiment of a condenser in accordance with the present technology.
Figure 3D:
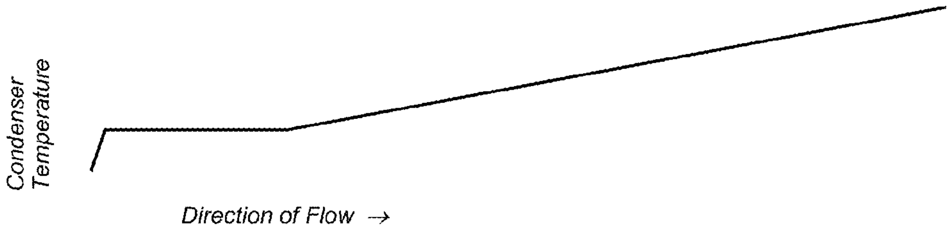
FIG. 3*d* is a plot of a temperature profile for the condenser designs of FIG. 2*d*.

A fourth aspect of the technology uses a short, warm wet-walled initiator, much as that described above, followed by a longer wet-walled section with a linear temperature ramp along its length. The walls are wetted throughout. This is illustrated in FIG. 2*d*. The corresponding temperature profiles are given in FIG. 3*d*. This aspect of the technology can provide a long spatial extent of uniform saturation conditions along each flow trajectory. It is designed to accommodate those species that are not readily activated due to their hydrophobic nature, and require more time within the region of supersaturation to activate.

The second, third and fourth aspects of the technology can be combined with the sizing of the condenser developed under the first aspect, to provide for uniform performance over a range of particle concentrations. These condenser designs can be used with either the differentially diffusive approach wherein the flow enters a warm, wet-walled condenser, or the diffusive mixing approach wherein a warm saturated sheath flow is introduced around the aerosol flow. All of these aspects are applicable to multiple geometries, including tubes or parallel plates, or to slightly converging tubes or parallel plates.

Performance of each of these configurations can be understood using a numerical model that accounts for the details of the droplet growth. This numerical model of laminar flow condensation systems includes the condensational heat release and vapor depletion associated with droplet formation, that allows wall temperatures to vary along the length of the flow, and accommodates either cylindrical tubes or parallel plate geometries.

In accordance with this numerical model the temperature (T) and water vapor concentration (c) are solutions to the stationary convection-diffusion equation, $$v\cdot\nabla T=\alpha\nabla^2 T \qquad \text{(Temperature)}$$

$$v\cdot\nabla c=D\nabla^2 c \qquad \text{(Water vapor concentration)}$$

where α is the thermal diffusivity of air, and D the molecular diffusivity of water vapor in air. In a cylindrically symmetric system, assuming the velocity v is solely in the z direction and has a fully-developed parabolic flow profile, the temperature equation becomes $$2U[1-(r/R_0)^2]\frac{\partial T}{\partial z}=\alpha\left(\frac{1}{r}\frac{\partial}{\partial r}\left(r\frac{\partial T}{\partial r}\right)+\frac{\partial^2 T}{\partial z^2}\right), \qquad (1)$$

where r and z are radial and axial coordinates, respectively, $R_o$ is tube radius, and U is average flow velocity. For a parallel plate geometry, the equation becomes $$\frac{3}{2}U[1-(x/X_0)^2]\frac{\partial T}{\partial z}=\alpha\left(\frac{\partial^2 T}{\partial x^2}+\frac{\partial^2 T}{\partial z^2}\right), \qquad (2)$$

where z is in the direction of the flow, x is perpendicular distance from the centerline and $\delta=2X_o$, is the separation between the plates. The third dimension, the overall width of the plates, is assumed infinite. Fluid properties evaluated at a mean temperature are treated as constants over the domain.

Profiles of the water vapor concentration, c, are determined by the analogous equations with a replaced by molecular diffusivity D, and T replaced by concentration c. The saturation ratio S is defined as the ratio between the partial pressure of water vapor and the equilibrium water vapor pressure associated with the local temperature.

At the wetted surface, the boundary conditions (for the tube) are given by:

$$c(R_0)=c_{sat}(T_{wick}(z))$$

$$T(R_0)=T_{wick}(z)$$

where $T_{wick}$ is the temperature profile of the wetted surface (e.g., cold, transitioning to hot) and $c_{sat}(T_{wick})$ is the water vapor concentration corresponding to a dew point of $T_{wick}$ (100% RH).

A quantity important to the activation of condensational growth is the Kelvin equivalent diameter. This is calculated at each point from the saturation ratio and temperature profiles and the properties of the condensing vapor. The Kelvin equivalent diameter is defined as:

$$d_K = \frac{4\sigma_s M_w}{\rho R_g T \log S} \quad (3)$$

where $M_w$, ρ and $\sigma_s$ are the molecular weight, liquid density and surface tension of water, $R_g$ is the universal gas constant, T is the absolute temperature, and S is the water vapor pressure saturation ratio. The Kelvin equivalent diameter corresponds to the diameter of a water droplet whose equilibrium vapor pressure is given by the saturation ratio S. For particles, the activation diameter also depends on particle chemistry. For particles composed of a material that is not wetted by the condensing vapor, the activation diameter will be larger than $d_K$. For soluble particles, dissolution into the condensate on the particle surface lowers the equilibrium vapor pressure; and the critical diameter required for particle growth is smaller, as described by the Raoult term in the Köhler equation.

After the temperature and vapor concentration fields have been calculated, the droplet growth is evaluated by numerically integrating the growth rate along its trajectory. Although the droplet's size and environment are changing as it is carried through the condenser, that timescale is long compared to the time required for a droplet to equilibrate with its surroundings. Therefore, when calculating the growth rate of a droplet at some point along its trajectory, an approximation is used that its properties are in a steady state and that it exists alone in an infinite volume.

With the steady state assumptions the rate of change of the radius a of the droplet is given by $$\frac{da}{dt} = \frac{D}{\rho}\frac{(c_\infty - c_s)}{a}\Phi(a),$$

where $c_\infty$ is the water vapor concentration far from the droplet (which is simply the quantity c from the convection-diffusion equation) and $c_s$ is the concentration at the surface. The factor $(c_\infty - c_s)/a$ is the concentration gradient resulting from a spherically-symmetric diffusion process. The value of $c_s$ is determined by the saturation vapor pressure of water, taking into account the temperature at the droplet surface, $T_s$, and the Kelvin relation:

$$c_s = \frac{p_{sat}(T_s)}{R_g T_s}\exp\left(\frac{4\sigma_s M_w}{\rho R_g T_s}\right)$$

The Φ(a) term is a correction term to provide continuity between the free molecular and continuum regimes. The Fuchs-Sutugin correction method is used with the accommodation coefficient equal to one:

$$\Phi(a) = \frac{1 + Kn}{1.33Kn^2 + 1.71Kn + 1}$$

where the Knudsen number, Kn=λ/a, is the ratio of the mean free path to the particle radius. The mean free path is given by $\lambda = 3D/\bar{c}$, where $\bar{c}$ is the mean molecular speed.

The droplet temperature is handled with the same quasi-steady-state approach. Heat is added or lost via a thermal gradient term. Additionally, a concentration gradient, which implies growth, contributes condensational heat:

$$\frac{\rho C_p a}{3}\frac{dT_s}{dt} = k_v\frac{T_\infty - T_s}{a} + H_{vap}D\frac{(c_\infty - c_s)}{a}$$

where $k_v$ is the thermal conductivity of the vapor phase, $H_{vap}$ is the heat of vaporization of water and $T_\infty$ is the temperature far from the droplet—in other words, T from the convection-diffusion equation. These relations for droplet temperature and size are solved numerically by taking small steps forward in time along the stream line, with the assumptions of constant fluid properties and rapid temperature equilibration within the droplet.

Finally, the effects of high number concentrations are handled in an iterative fashion. After the droplet growth has been calculated, the depletion of the vapor and the condensational heat are added into the convection-diffusion equation. The growth and diffusion calculations are iterated to find a self-consistent result.

Our numeric solution was developed using Crank-Nicholson approach for the integration of the diffusion equations. The model was validated against the analytical, series solution of Stolzenburg and McMurry (M. Stolzenburg and P. McMurry, An ultrafine condensation nucleus counter, Aerosol Science and Technology 14: 48-65, 1991) in the limit of low particle concentrations, and constant wall temperatures.

Using the above modeling, one can provide design criteria for producing consistent saturation profiles over a wide range of sampled particle concentrations in a variety of laminar flow water condensation system configurations. With similar saturation profiles over a range in particle concentrations the shifts in the smallest detectable particle size are minimized, and the droplet growth is more consistent. Shown below, a single stage condenser is first examined, although the concepts developed also apply to the multi-stage condensers introduced here.

Figure 4A:
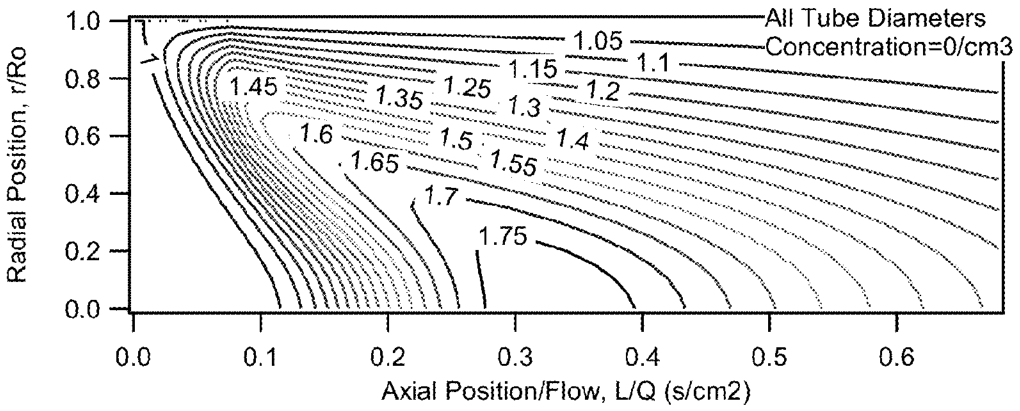
FIG. 4*a* is a plot showing saturation profiles of radial position relative to axial position within a cylindrical, single-stage condenser at a first particle concentration and various condenser diameters.
Figure 4B:
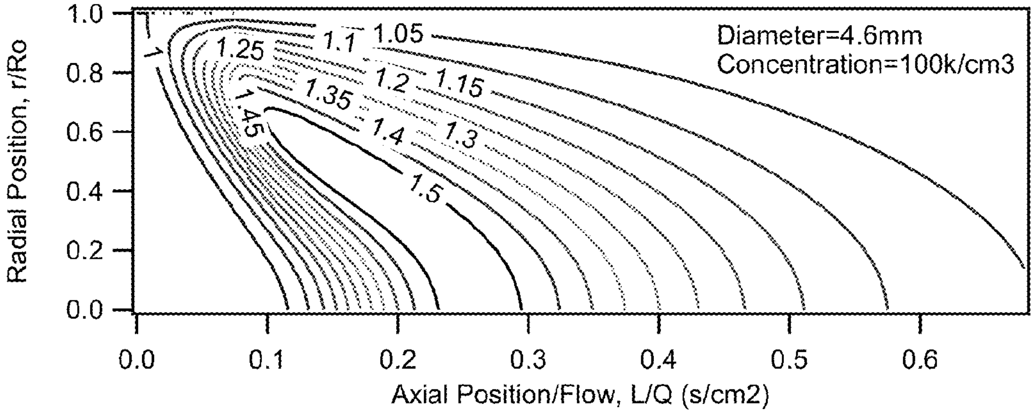
FIG. 4B is a plot showing saturation profiles of radial position relative to axial position within a cylindrical, single-stage condenser at a second particle concentration and a 4.6 mm diameter.
Figure 4C:
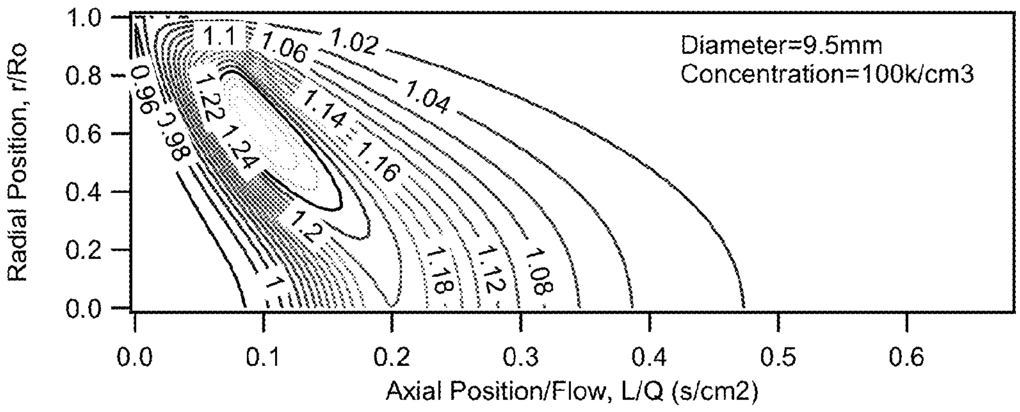
FIG. 4*c* is a plot showing saturation profiles of radial position relative to axial position within a cylindrical, single-stage condenser at the second particle concentration and a 9.5 mm diameter

The first aspect of the technology is illustrated in FIG. 4. The calculated saturation profile within the single stage condenser of FIG. 2*a*, having a constant wall temperature as shown in FIG. 3*a*, is shown in FIG. 4*a*. The flow direction is from left to right, and the centerline is along the bottom axis. The radial coordinate r is normalized by the tube radius Ro. Because the flow is symmetric, only the one-half of the profile is plotted, from the centerline (r/Ro=0) to the edge (r/Ro=1). The axial coordinate, that is the dependence along the direction of flow, is divided by the volumetric flow rate. These calculations are for a cylindrical geometry with diameter 2Ro, where the flow enters the condenser at 20° C. and 100% RH, and that the wetted walls of the condenser are at 60° C. Similar results have been found for other operating conditions.

At very low particle concentrations the saturation profiles are independent of the tube diameter, and the profiles of FIG. 4*a* applies to both the narrow and wide bore tubes. The axial dependence varies as the ratio of the axial position to the volumetric flow rate, a result that is seen by expressing the convective diffusion equations in nondimensional form. Thus at twice the volumetric flow rate the profiles stretch so that when plotted as shown the profile does not shift, but a tube of twice the length is required to encompass the entire profile. The maximum saturation is along the centerline at an axial distance to flow rate ratio of 0.32 s/$cm^2$. Similar results have been found for other operating conditions. Although the time required to move from one contour to the next is independent of the flow rate, this transit time does increase with increasing the tube diameter.

Residence time, and hence tube diameter, is important to consider in the droplet growth. As seen by comparing FIG. 4*b* and FIG. 4*c*, the saturation profiles that are found when the concentration of activated particles reaches $10^5$/$cm^3$ are more greatly shifted from the near-zero concentration case of FIG. 4*a* when the tube diameter is larger. This is due to the larger residence time for the wider bore tube, which creates larger droplets with correspondingly more condensational heat release. The smaller diameter tube limits the time for growth, thereby reducing the amount of condensational heat release and vapor depletion, and provides a more consistent performance over a range of particle concentrations.

Figure 5A:
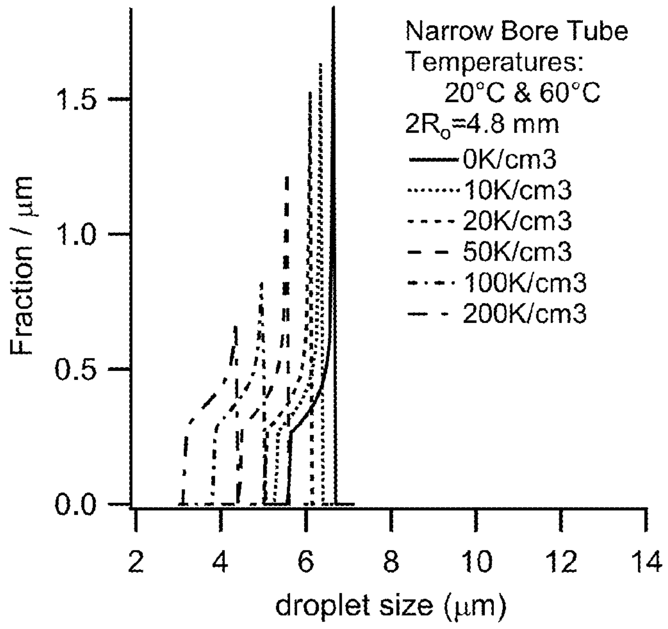
FIG. 5*a* is a graph showing the calculated droplet sizes exiting a single-stage condenser at a first t condenser diameter.
Figure 5B:
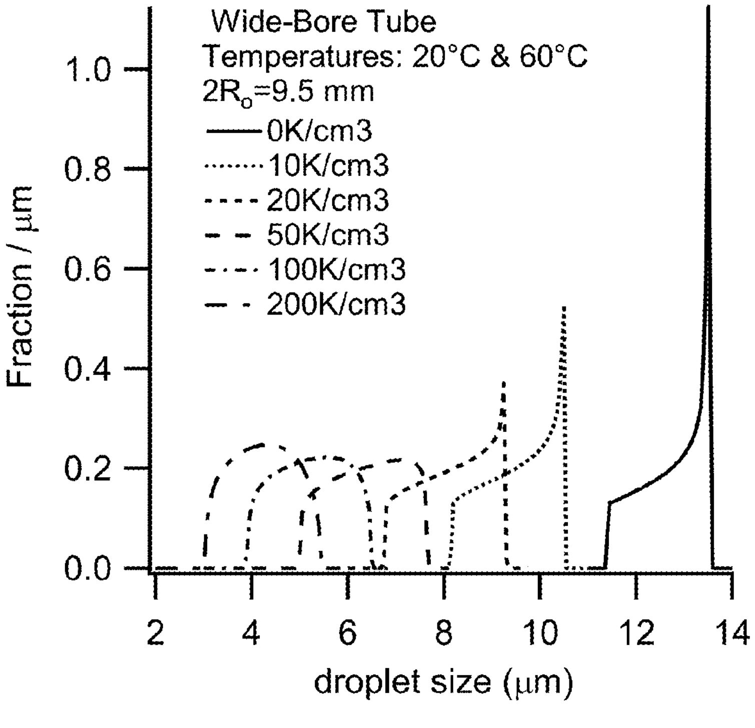
FIG. 5*b* is a graph showing the calculated droplet sizes exiting a single-stage condenser at a second condenser diameter.

FIG. 5*a* shows the droplet sizes for the narrow bore tube calculated by the model for concentrations of activated particles ranging from near-zero to $2\times10^5$/$cm^3$. FIG. 5*b* shows the same calculation for the wide-bore tube. The condensational heat release from water condensation during droplet formation warms the flow, and thereby increases the equilibrium vapor concentration and decreases the saturation ratio. For the wide-bore tube of the original implementation, higher the concentrations produce smaller droplets. For the narrow-bore tube of the current "kinetically limited growth" the shift in droplet size is much reduced. At high concentrations the narrower tube produces nearly the same droplet size as the wide-bore tube, but at low concentration its droplet size is approximately half of that from the wider tube. The result is a much narrower overall range in droplet size as a function of the number concentration of the activated particles.

Figure 6:
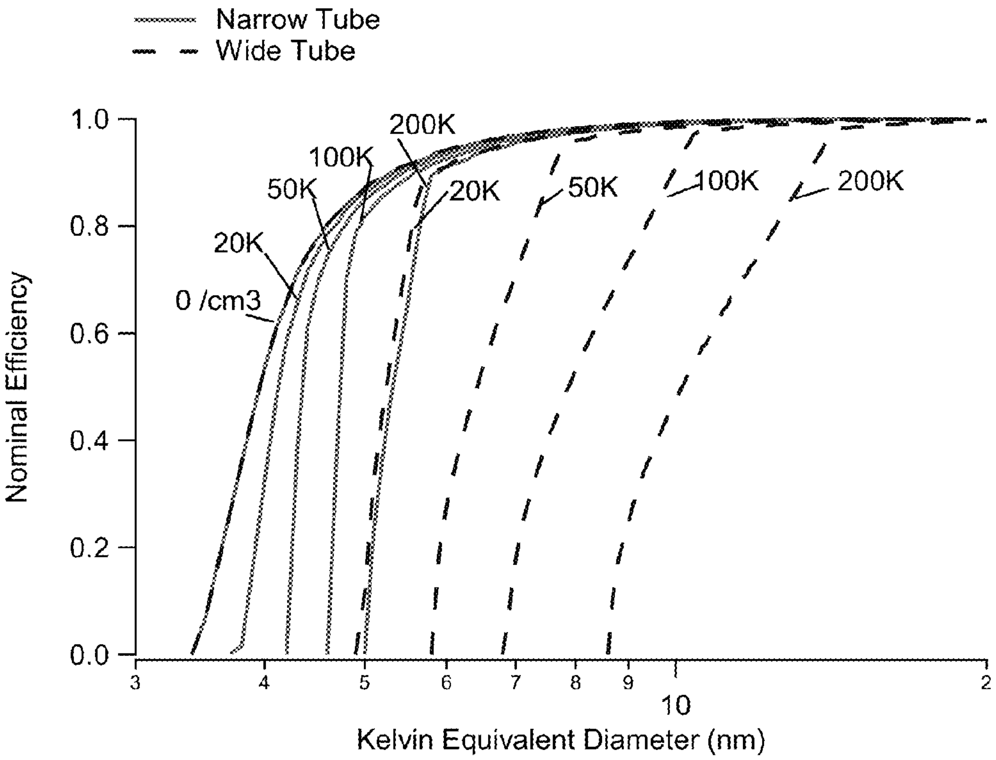
FIG. 6 shows the Kelvin equivalent diameter, which is related to the activation diameter, for two single-stage condensers of two different condenser diameters, and for different number concentrations of activated particles.

Another consequence of the decreased saturation ratio at higher particle concentrations is an increase in the activation diameter. The activation size, which refers to the smallest particle that will be grown by condensation, depends on the difference in Gibbs free energy between the liquid and vapor, which in turn depends properties of the vapor (surface tension, saturation ratio and temperature) as well as properties of the particle (solubility, wetability). The Kelvin equivalent diameter, defined by equation (3) describes the minimum size of a water droplet that would be more likely to grow than to shrink, and characterizes much of the vapor properties important to activation. Each flow streamline has a characteristic minimum Kelvin equivalent diameter along its trajectory, from which one can derive the fraction of the flow as a function of the minimum Kelvin equivalent diameter encountered. FIG. 6 shows how this shifts as a function of the number concentration particles that activate, and the diameter of the growth tube. As with the droplet diameter, the shift is most pronounced for the larger tube diameter.

Figure 7A:
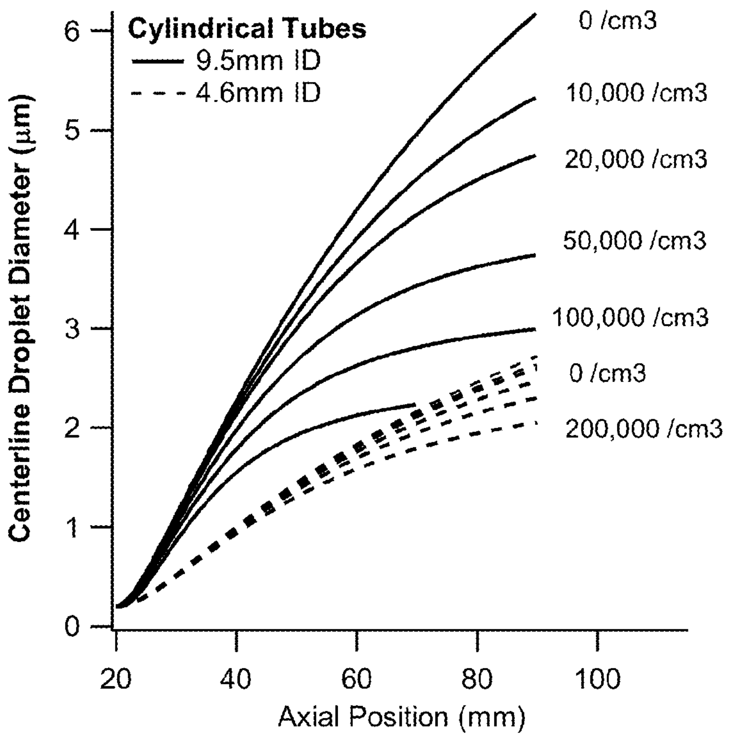
FIG. 7*a* is a graph for droplet diameter versus axial position showing the evolution of droplet diameter along the direction of the flow for the single-stage condenser for cylindrical geometry of varying dimensions.
Figure 7B:
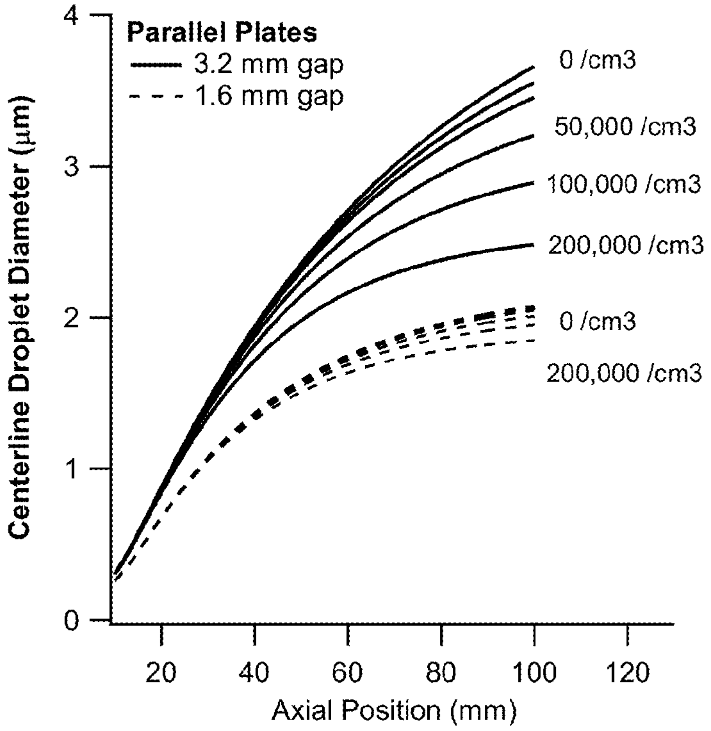
FIG. 7*b* is a graph for droplet diameter versus axial position showing the evolution of droplet diameter along the direction of the flow for the single-stage condenser for parallel plate geometry of varying dimensions.

FIG. 7*a* and FIG. 7*b* compare model results for cylindrical and parallel plate geometries. Here the evolution in droplet size along the centerline flow trajectory is shown. Growth is largest along the edge, where residence time is longer. For all flow trajectories the droplet growth is significantly less at high particle number concentrations. This adverse effect is minimized by the use of a narrow-tube condenser, as in FIG. 7*a*, or by more closely spaced parallel plates, as in FIG. 7*b*.

Many different operating configurations, including both upward and downward temperature ramps, and parallel plate as well as cylindrical geometries, have been investigated and proven useful. All are incorporated as part of the present disclosure. While the droplet size at low concentration can be varied, the fundamental result was unchanged. Those conditions which produce large droplets at low particle concentrations showed pronounced concentration effects, with large decrease in the droplet size with increasing particle concentrations. Narrower tubes or more closely spaced plates that produce smaller droplets at low concentrations showed less decrease in droplet size with increasing concentration such that the droplet sizes at high concentrations are nearly equivalent. The use of the narrower dimensions provides less time for the droplets to grow, and hence kinetically limit the growth at low particle concentrations. At higher concentration the growth is limited by the condensational heat release. Our analysis shows that for water condensation systems, the reduction in saturation ratio at high particle concentrations is mostly due to condensational heat release, with a small contribution from vapor depletion.

The second embodiment of the technology replaces the single-stage condenser of FIG. 2*a* with a two-stage condenser as shown in FIG. 2*b*. This two-stage condenser consists of a short warm-walled "initiator" followed by a cold-walled "equilibrator". The combined length of the initiator and equilibrator is approximately the same as for the single-stage condenser. The walls of the initiator are warmer than the temperature of the entering flow. Generally, this is accomplished by using a preconditioner ahead of the initiator which has walls at a temperature lower than the temperature of the initiator. The walls of the equilibrator are at a lower temperature than the walls of the initiator section, but can be either warmer or cooler than the preconditioner. The walls of both the initiator and equilibrator are wetted. This condenser design may be used with either parallel plate or tubular configurations, and with either the differentially diffusive or diffusive mixing technology.

In one embodiment, one can maintain warm wetted walls throughout the condenser in order to promote the droplet growth. However, in alternative embodiments, this is not necessary. The saturation ratio along the centerline is nearly the same if a long, single stage condenser is used, or if an appropriately sized two-stage growth region consisting of a short warm-walled section (the initiator) followed by a cold-walled section is used.

Figure 8A:
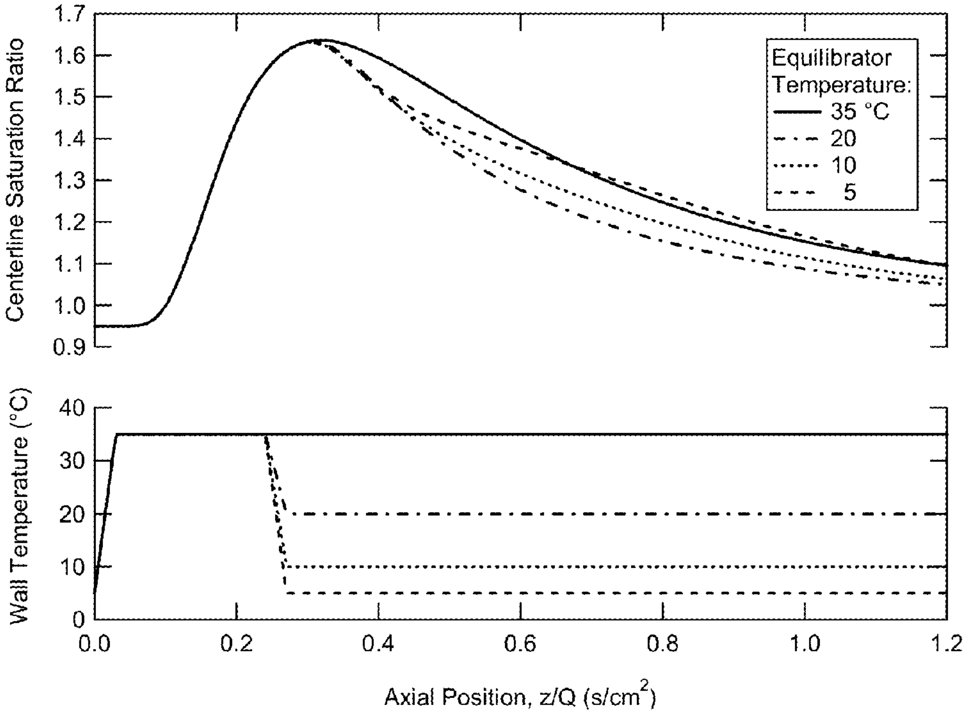
FIG. 8*a* is a graph showing the centerline saturation ratio, wall temperature and axial position showing droplet growth for various configurations of the two stage, initiator-equilibrator condenser configuration.
Figure 8B:
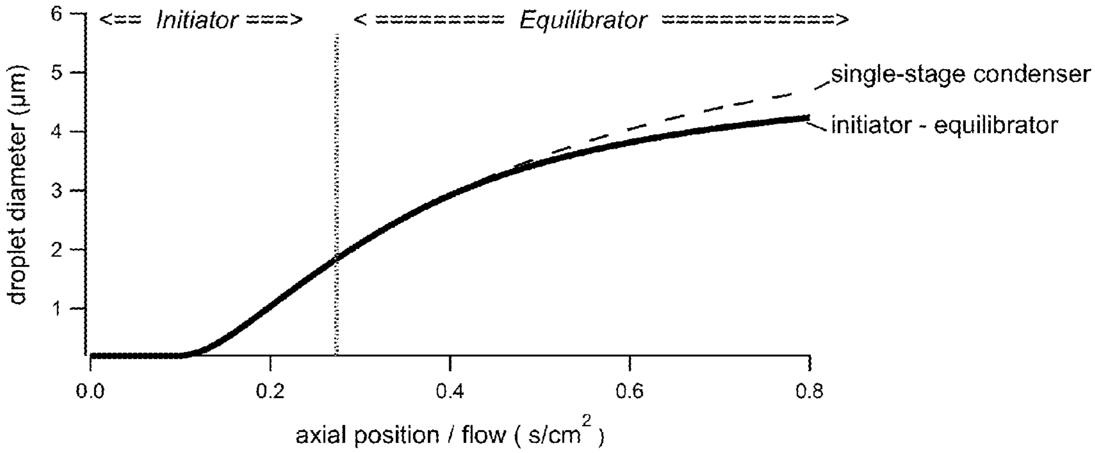
FIG. 8*b* is a graph of the droplet diameter versus the axial position comparing a single stage condenser to the present technology.

FIGS. 8*a* and 8*b* compares the centerline saturation ratio calculated for a 5° C. flow entering a 35° C. initiator, followed by an equilibrator operated a various wall temperatures. The walls are wetted throughout. Calculations at a downstream wall temperature of 35° C. correspond to the single stage condenser, while the other lower downstream temperatures describe various configurations of the initiator-equilibrator condenser. In all cases the length of the initiator divided by the air flow rate passing through it is 0.24 s/$cm^2$. This length was selected to be just long enough to provide the same maximum saturation ratio as obtained with the single stage condenser. The calculations for FIG. 8 correspond to for low particle concentrations, when condensational heating and vapor depletion are ignored. The calculations presented are for a cylindrical geometry. In the limit of low particle concentrations, the temperature and saturation profiles depend on the ratio of the axial length to the volumetric flow through the tube, and are independent of the tube diameter. Thus the results are plotted as a function of the ratio of the axial position to the volumetric flow rate through the tube, where the axial position is defined as the distance downstream from the entrance of the initiator.

As shown in FIG. 8*a*, the saturation ratio along the centerline is relatively insensitive to the wall temperature of the equilibrator. Moreover, the maximum saturation occurs downstream of the initiator, at an axial position to flow rate ratio of 0.32 s/$cm^2$. This is because it takes some time for the water vapor to be transported from the walls of the initiator to the centerline of the flow, during which time convection carries the water vapor downstream. Further downstream the flow cools, and water vapor is removed by the cold wall. The relative rate of these two processes is such that the removal of water vapor is offset by the reduction of equilibrium vapor pressure due to cooling with the result that the saturation ratio profile is nearly the same for all selected operating temperatures within the equilibrator.

Because the droplet growth is driven by the saturation ratio, the droplet growth is similar to that for the single-stage condenser. FIG. 8*b* compares the centerline modeled droplet growth for the initiator-equilibrator configuration to that modeled for single-stage condenser. The calculations are for a cylindrical geometry with an airflow at 5° C. that enters an initiator with 35° C. wetted walls followed by an equilibrator with 20° C. wetted walls, or that enters a single-stage condenser with wetted walls at 35° C. As in FIG. 8*a*, the length of the Initiator divided by the volumetric flow rate is 0.24 s/$cm^2$. The length of the Equilibrator that follows, when divided by the volumetric flow, is 0.56 s/$cm^2$. The length of the single-stage condenser divided by the volumetric flow rate is 0.8 s/$cm^2$. The droplet size that exits at the end of the initiator-equilibrator configuration, with its short warm section followed by a longer cold section, is nearly the same as for the single-stage condenser, with warm walls throughout. As illustrated by these results, most of the droplet growth occurs in the equilibrator section. The initiator by itself is too short to serve the function of the single-stage condenser. It is the combined initiator-equilibrator that provides both the activation of condensation and the time for the droplet growth.

Figure 9A:
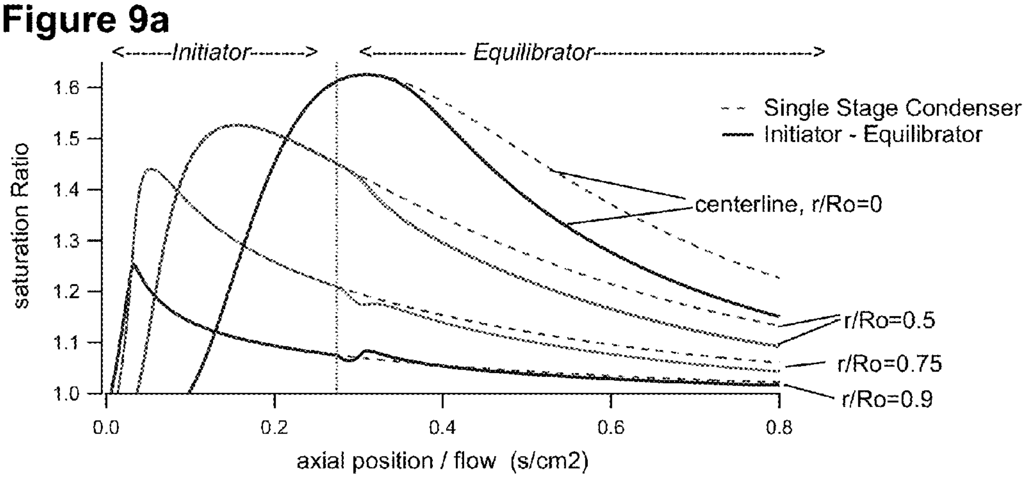
FIG. 9*a* compares the saturation ratio, FIG. 9*b* the temperature and FIG. 9*c* the water vapor=relative to the axial position—for content obtained using the initiator-equilibrator configuration to that found with the single stage condenser.
Figure 9B:
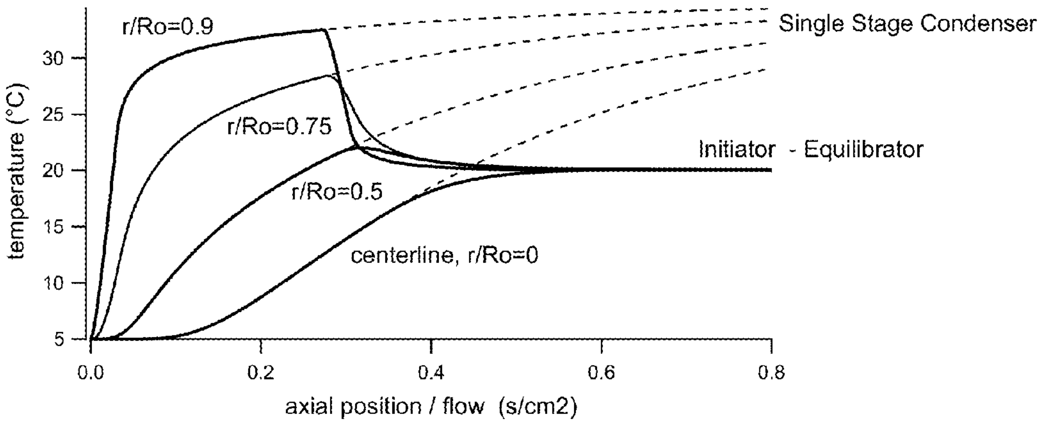
Figure 9C:
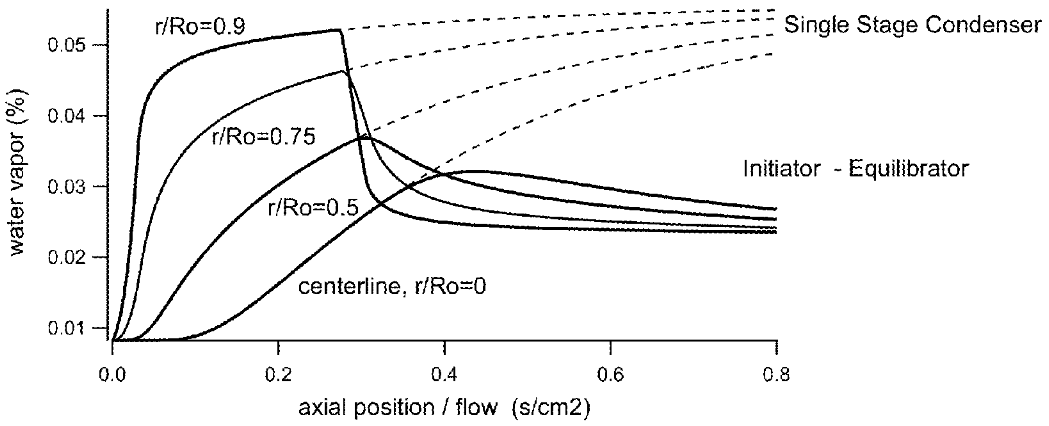

FIGS. 9*a*, 9*b* and 9*c* provide further detail for the specific case when an equilibrator operated at 20° C. is coupled to a short, 35° C. Initiator. Again, calculations are done for an flow entering flow is at 5° C. Comparison is given to a single-stage condenser with wetted 35° C. walls throughout. Shown is the saturation ratio, temperature and water vapor content along 4 trajectories, from the centerline (r/Ro=0) to near the edge of the tube (r/Ro=0.9). For fully developed laminar flow approximately half of the flow volume is contained between the trajectory at r/Ro=0.5 and the centerline.

FIG. 9*a* shows that at all radial positions the peak supersaturation is the same for the initiator-equilibrator as for the single stage condenser. This implies that the activation of particle condensational growth will be the same as for the single stage condenser. However both the temperature and water vapor content are much reduced.

As shown in FIG. 9*b*, the exiting temperature is close to the wall temperature. Moreover, the centerline temperature never exceeds the equilibrator wall temperature, and midpoint temperature never climbs above 22° C. Thus most of the flow is not significantly heated by the initiator, an important aspect when handling semi-volatile materials. In contrast, with the single stage condenser the flow continues to warm after reaching its peak supersaturation, with exiting temperatures between 29° C. and 34° C. As shown in FIG. 9*c*, in this example the use of the initiator-equilibrator in place of the single stage condenser reduces the water vapor content by a factor of about two. This can be reduced further by selecting a yet colder wall temperature for the equilibrator. With the single stage condenser water vapor is continually added to the flow throughout the growth region. In contrast, with the initiator-equilibrator, water is only added to the flow when passing through the Initiator. In addition, some of the water vapor is removed within the equilibrator. With the reduced water vapor content it is possible to collect, or focus or detect the droplets that are formed without complication from condensation. Specifically, for the example given, it would possible to avoid condensation by operating the downstream components at a moderate ~21° C. instead of the 35° C. that would be required of the single stage condenser.

Figure 10:
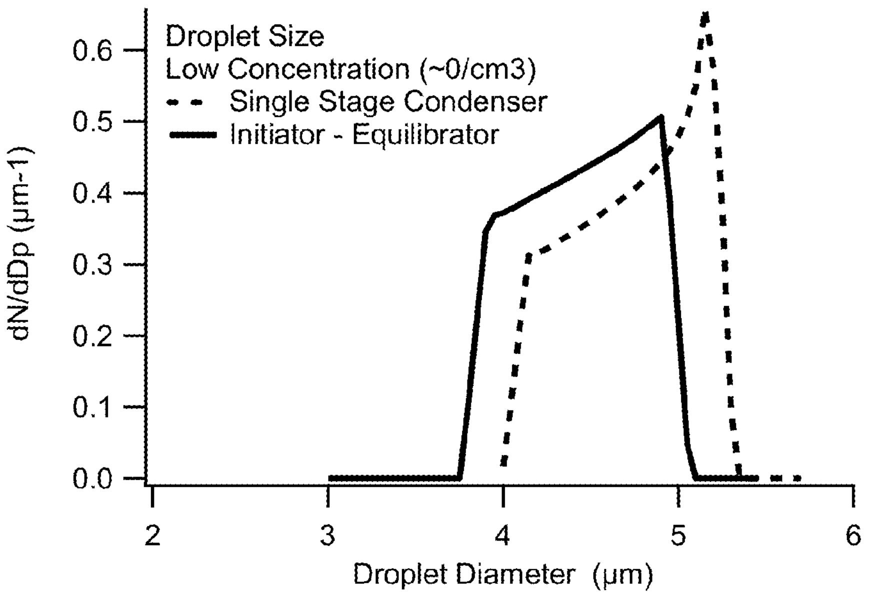
FIG. 10 compares the exiting droplet size obtained using the initiator-equilibrator configuration to that found with the single stage condenser.
Figure 11:
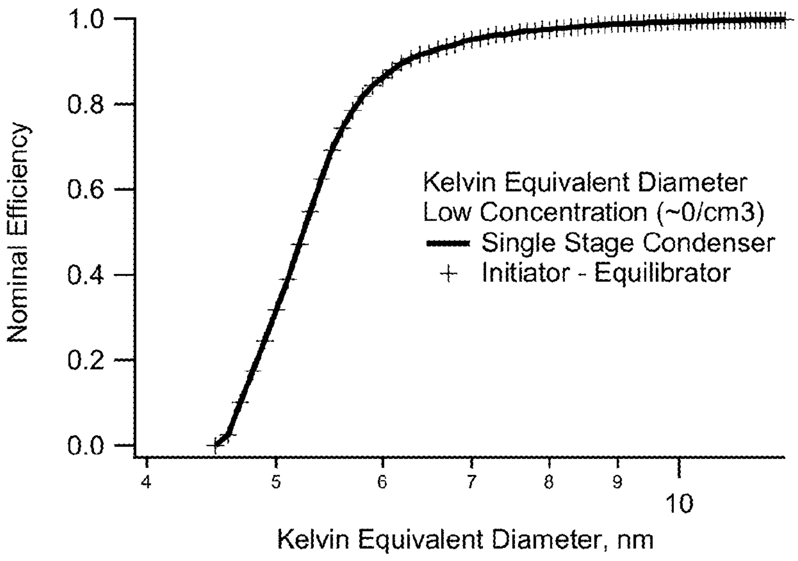
FIG. 11 compares the Kelvin equivalent diameter obtained using the initiator-equilibrator configuration to that found with the single stage condenser.

FIG. 10 compares the droplet size produced by the initiator-equilibrator approach to that of the single stage condenser at low particle concentration. FIG. 11 compares the activation conditions, as indicated by the Kelvin equivalent diameter for these two configurations. These calculations are done for the same conditions as those for FIG. 9, with a humidified 5° C. flow entering either a single-stage, 35° C. wet walled condenser, or entering a 35° C. wet walled initiator followed by a 20° C. equilibrator. These calculations show that the size of the droplets formed is only slightly smaller, while the activation conditions are identical.

Figure 12A:
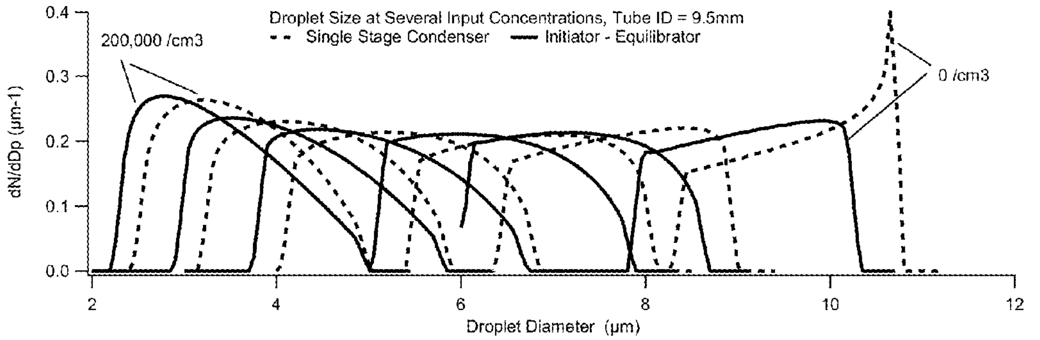
FIG. 12*a*-12*c* compare the droplet sizes obtained using the initiator-equilibrator configuration to that found with the single stage condenser over a range of particle concentration and tube diameters, where
Figure 12B:
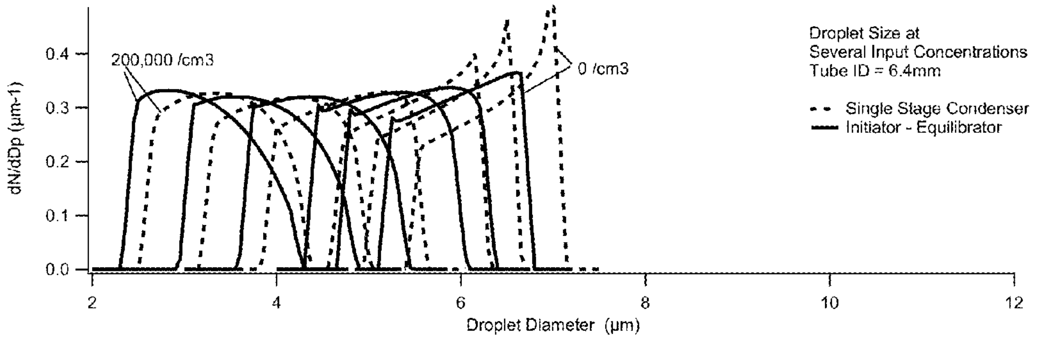
Figure 12C:
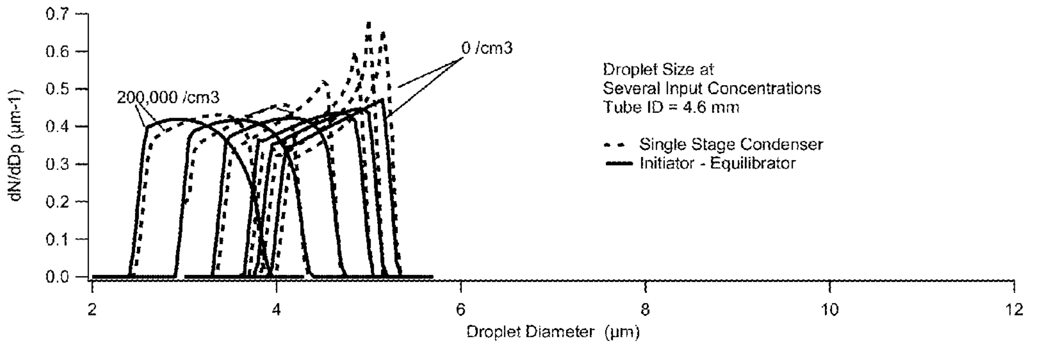
Figure 13:
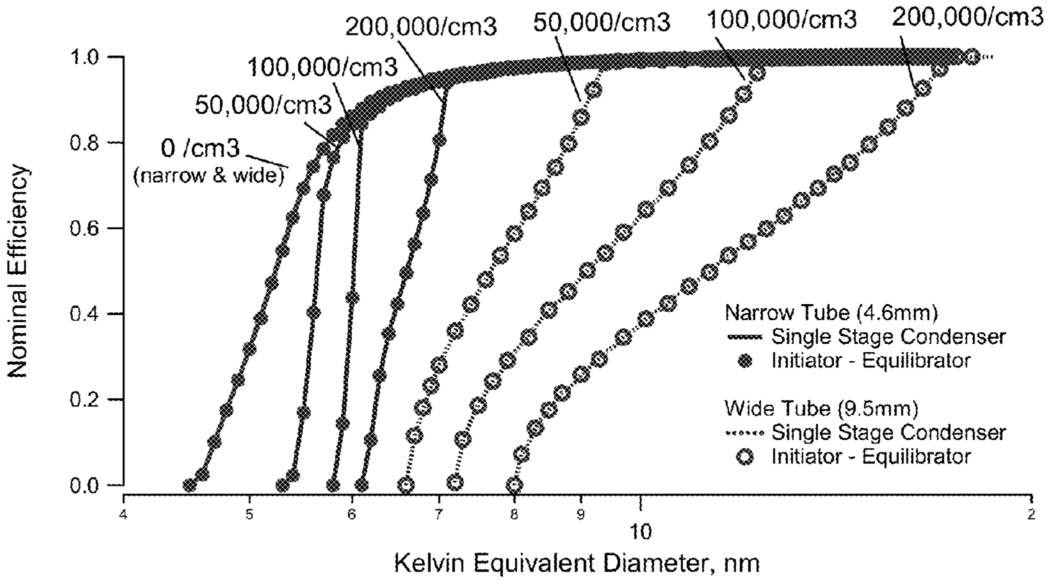
FIG. 13 compares the Kelvin equivalent diameter obtained using the initiator-equilibrator configuration to that found with the single stage condenser over a range of particle concentrations, for two tube diameters.

FIGS. 12 and 13 show the effect of the sampled particle number concentration on droplet size and on the activation size. As in the first aspect of this technology, the droplet size decreases and the Kelvin equivalent diameter increases with increasing particle number concentration. Primarily this is due to the warming of the flow from condensational heat release. Exactly as described above, the concentration effects are minimized by employing narrower tubes. FIG. 12*a* presents the calculated droplet diameters with and without the equilibrator, when the diameter of the condenser tube is 4.6 mm. FIG. 12*b* shows these results for a condenser 6.3 mm diameter condenser, and FIG. 12*c* shows these results for a 9.5 mm diameter condenser. For the wide-bore tube the median droplet size varies from 10 μm to 3 μm, while for the narrow tube it varies from 6 μm to 3 μm. The narrower tube kinetically limits the droplet growth at low concentrations, providing more uniform overall droplet diameters. Similarly, the narrower tube minimizes the shift in the particle activation conditions, as indicated by the Kelvin diameter. Thus the optimal implementation of the technology is the combination of the narrow flow dimensions of the first aspect, with the initiator-equilibrator growth region of this aspect.

Figure 14A:
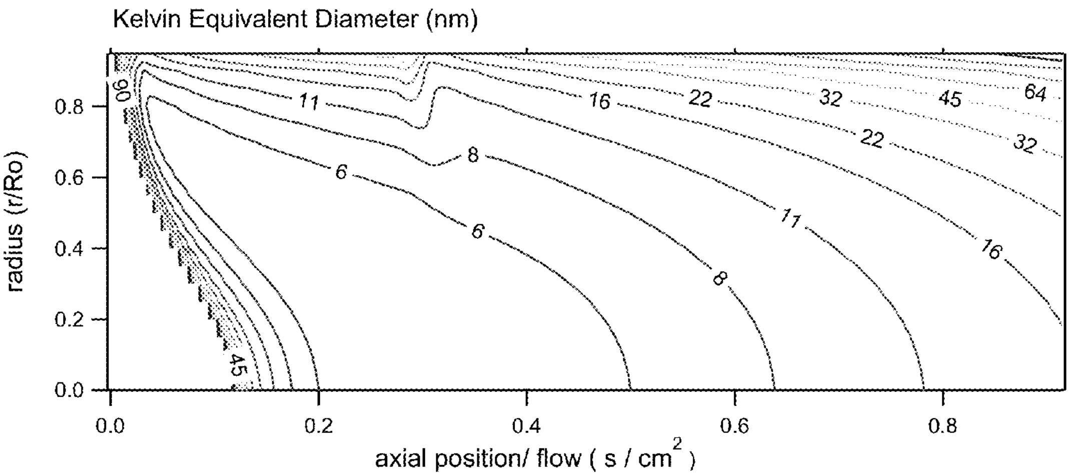
FIG. 14*a* shows profiles of the Kelvin equivalent diameter and FIG. 14*b* the dew point for the initiator-equilibrator configuration of the present technology applied to a diffusive mixing approach of U.S. Pat. No. 7,736,421.
Figure 14B:
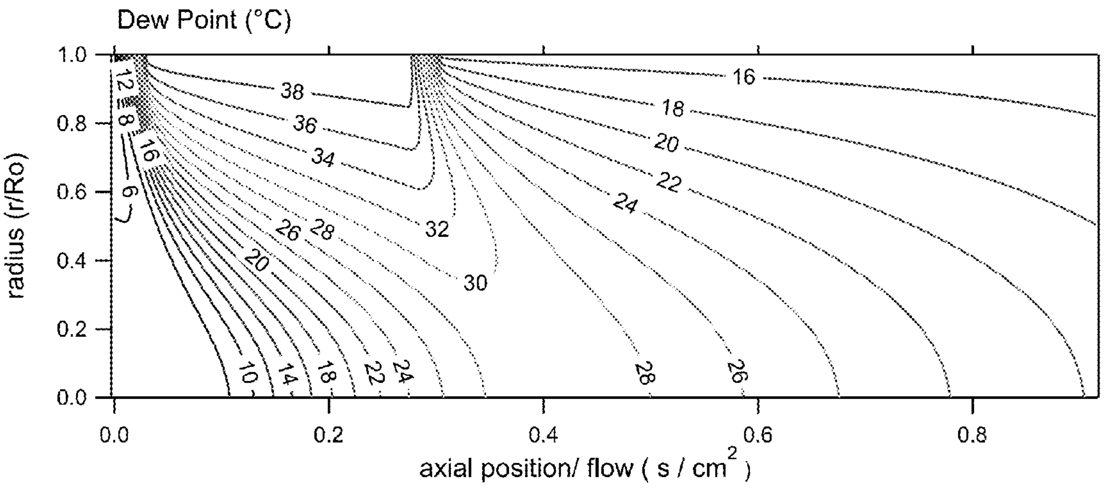

The initiator-equilibrator technology (FIG. 2*b*) is also applicable to the diffusive mixing concept of U.S. Pat. No. 7,736,421. Here a warm saturated flow is introduced in a sheath around the cold aerosol flow at the entrance of the initiator. The merged flows pass through the initiator and the equilibrator. As before one may use a short initiator, with a length to volumetric flow rate ratio of 0.25 s/$cm^2$. In this case the saturated sheath and initiator wall temperatures are both set to 40° C., and the Equilibrator wall temperature is 15° C. The entering flow is at 5° C. FIG. 14*a* shows the profile of Kelvin equivalent diameters. FIG. 14*b* shows the dew point. A Kelvin equivalent diameter of 4.5 nm is achieved, which is similar to that for the original single stage condenser operated at these temperatures. With a narrow tube of 4.3 mm diameter the calculated final droplet size ranges from 5 μm at low concentrations to 3.5 μm at $2\times10^5/cm^3$, which again is similar to narrow tube of the original design. However, the exiting temperature and dew point of the exiting flow drops from near 40° C., to just below 20° C.

Figure 15A:
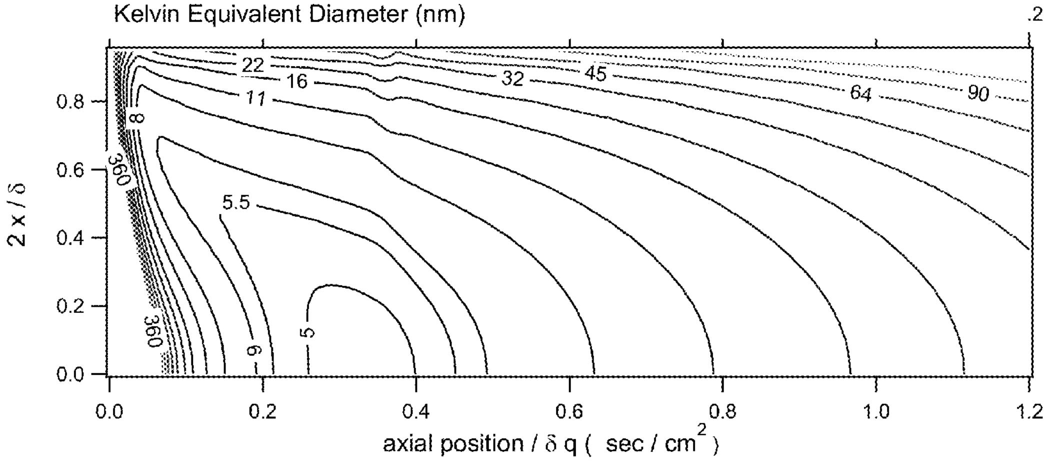
FIG. 15*a* shows profiles of the Kelvin equivalent diameter and FIG. 15*b* the dew point for the initiator-equilibrator configuration of the present technology applied to parallel plate configuration
Figure 15B:
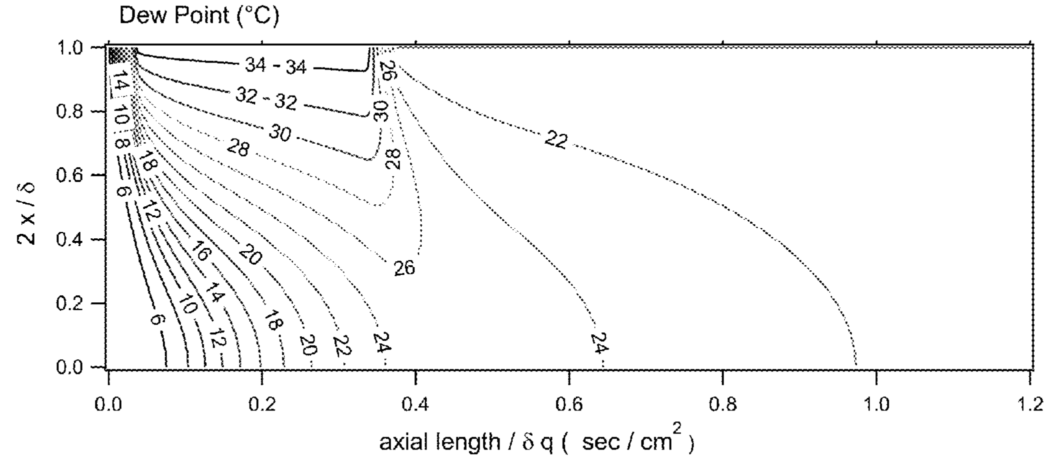

FIG. 15 shows the profiles of the Kelvin equivalent diameter and dew point obtained in the initiator-equilibrator for a parallel plate geometry. As before, the entering flow is humidified at 5° C., the walls of the Initiator are at 35° C. and the walls of the equilibrator are at 20° C. The axial scaling for the parallel plate geometry depends on the z/(q δ) where z is the coordinate in the direction of flow, q is the flow rate per unit width of the plates and δ is the gap width. In a simple parallel plate geometry, with a single stage condenser, the maximum supersaturation along the centerline occurs at an axial position of about z/(q δ)=0.3 $s/cm^2$ from the entrance of the condenser. As in the tubular geometry, one may use an initiator length that extends about three-quarters of the distance from the entrance of the growth region to the point of maximum centerline supersaturation, or z/(q δ)=0.25 $s/cm^2$.

Figure 16A:
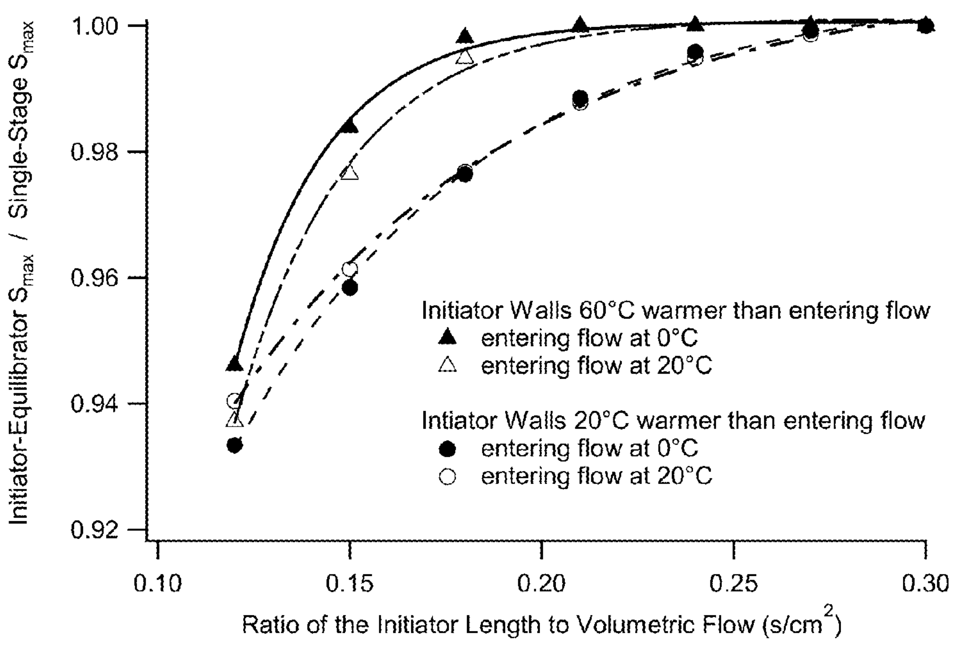
FIG. 16*a* shows the dependence of the maximum saturation ratio achieved as a function of the Initiator length divided by the volumetric flow rate for a cylindrical configuration.

FIG. 16*a* shows how the length of the initiator affects the peak supersaturation. For a cylindrical geometry, the plot, as a function of initiator length, is of the maximum supersaturation achieved divided by the maximum supersaturation that is produced by an infinitely long initiator operated at the same input flow and wall temperatures. The initiator length is expressed as the ratio of this length to the volumetric flow rate passing through the tube, as above, and the walls are wetted throughout. When the walls of the initiator are 60° C. warmer than the entering flow, an initiator length to flow rate ratio in the range from 0.16 to 0.17 $s/cm^2$ is sufficient to achieve 99% of the saturation ratio produced by an infinitely long wet walled tube. This range covers input flow temperatures ranging from 0° C. to 20° C. When the walls of the initiator are just 20° C. warmer than the entering flow, a somewhat longer initiator length to flow rate ratio of about 0.23 $s/cm^2$ is needed to achieve 99% of the maximum supersaturation for these operating temperatures. These parameters defining the initiator length apply to a wide range of equilibrator temperatures, ranging from a 5° C. to 20° C. below the initiator temperature.

Figure 16B:
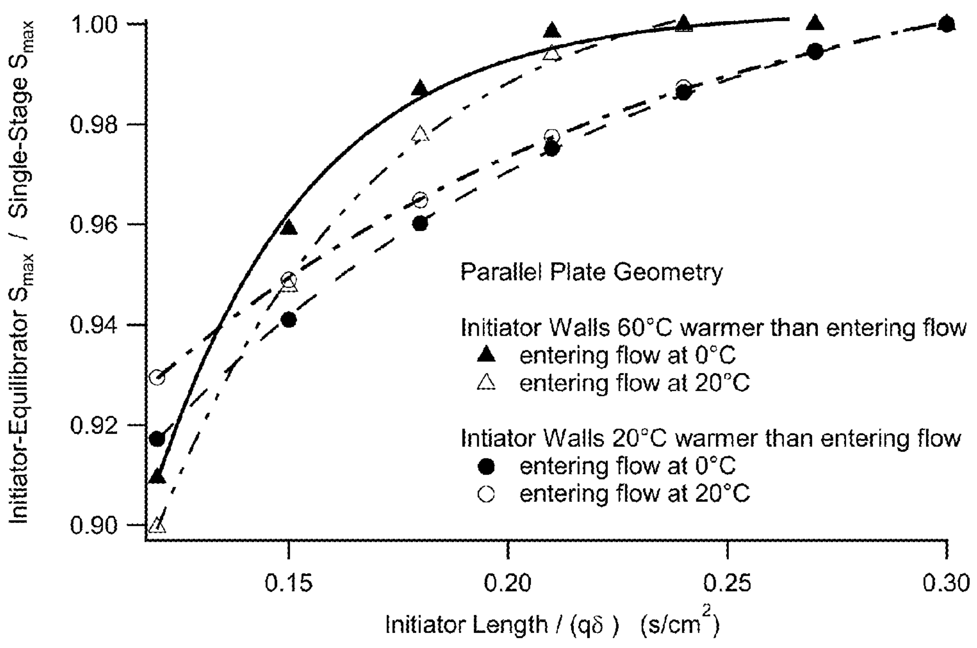
FIG. 16*b* shows the dependence of the maximum saturation ratio achieved as a function of the Initiator length divided by the volumetric flow rate for a parallel plate configuration.

FIG. 16*b* shows the analogous calculation for a parallel plate geometry, where the length of the initiator is now plotted as the ratio to the volumetric flow per unit width of the plates q multiplied by the plate separation δ, i.e. z/(qδ). The results are quite similar. When the wall temperature of the initiator is 60° C. above the temperature of the entering flow, a ratio of the initiator length to the quantity qδ of about 0.21 $s/cm^2$ is sufficient to achieve 99% of the saturation ratio possible with a single-stage condenser. As with the cylindrical geometry, somewhat longer initiator lengths are required when operating with a smaller temperature difference between the walls of the initiator and the flow the initiator-equilibrator condenser.

Hence, in a variety of geometries one is able to obtain the same particle activation diameters, and nearly the same droplet growth by using a two-stage condenser consisting of a short, wet-walled warm "initiator" followed by a longer colder-walled "equilibrator", as when using a single stage warm wet walled condenser of the same overall length. Further, the required length of the Initiator to achieve the same activation size as with a single stage condenser is about 75% of distance between the condenser inlet and the point of maximum supersaturation with single stage condenser. For the calculations presented here, with the warm part of the condenser walls 30° C. warmer than the preconditoiner, this corresponds to a length (0.25 $s/cm^2$)Q, where Q is the volumetric flow rate for a cylindrical geometry. Similarly for a parallel plate it is about (0.25 $s/cm^2$)(q/δ) where q is the volumetric flow rate per cm of plate width, and δ is the gap between the plates. This parameter shifts slightly with different operating temperatures or inlet conditioning, but generally is in the range from 0.1 to 0.3 $s/cm^2$. If a shorter initiator is used, the peak supersaturation will be somewhat lower that would be obtained with a longer one operated at the same temperature. If the initiator is longer, the peak supersaturation will not change, but the droplet size will be somewhat larger, but the subsequent equilibrator will still cool and reduce the water vapor content of the flow. With a relatively short initiator one can provide all of the water vapor necessary to create the same peak supersaturation as the longer single stage condenser. In the equilibrator that follows both the temperature and water vapor concentrations drop in a way that maintains a relative humidity very similar to that of the single stage condenser. This results in similar activation and growth but with a significant reduction in water vapor and temperature, and has many practical advantages when coupling detectors, focusing orifices or collectors.

The third aspect of the technology shown in FIGS. 2*c* and 3*c* utilizes a two-stage condenser system with an initiator followed by an "evaporator". It is designed for specialized applications wherein it is desired to create droplets of very uniform size and to evaporate them quickly. This is useful when a controlled and limited interaction between the droplets and material in the carrier gas is desired. The initiator is designed using the same criteria as in the second aspect of the technology, as described above. But instead of using the equilibrator to continue the droplet growth, one may instead use an evaporator that limits the maximum droplet size and then dries and evaporates the condensed water. Our modeling shows that this has the secondary advantage that it minimizes the dependence of droplet size on radial position, providing uniform maximum droplet sizes. As with the second aspect, this approach can be combined with the kinetically limited growth to provide consistent performance over a range of particle number concentrations.

Figure 17:
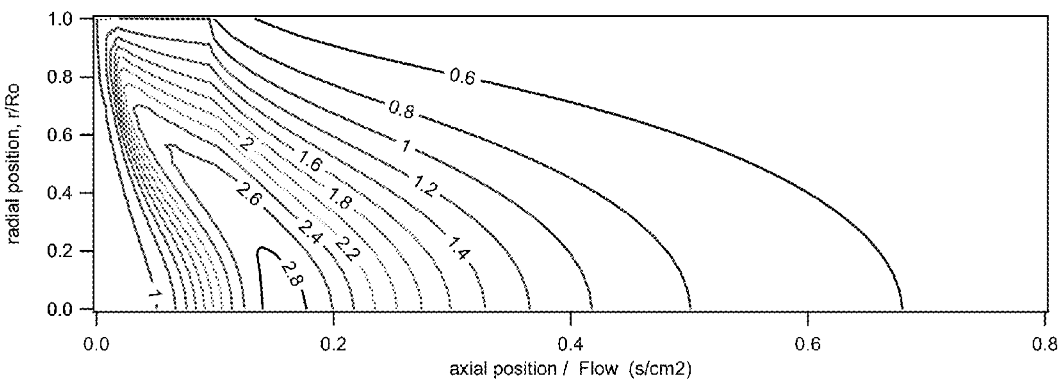
FIG. 17 shows the saturation ratio for the initiator-evaporator configuration.

As shown in FIG. 17, it is still possible to achieve quite high supersaturations with this approach. Plotted is the saturation profile obtained when a humidified air stream at 0° C. is introduced into a tube with walls at 50° C. The wet-walled Initiator has a scaled length to flow rate distance of 0.10 $s/cm^2$. The subsequent walls are held at the same temperature but are dry. In practice this is accomplished by lining the preconditioner and initiator sections with a wick that is in contact with a water reservoir, while leaving the evaporator walls bare. In the evaporator the walls will remain dry because the dew point of the flow is lower than the temperature of the walls. In this scenario, the peak centerline supersaturation is attained downstream of the end of the Initiator, at an axial position to flow rate of 0.15 $s/cm^2$. Again, because the water vapor concentration in the center of the flow is derived from an earlier portion of the flow, this provides for essentially the same activation efficiency as when the entire growth region has warm, wet walls. For the example presented the centerline saturation ratio reaches 2.9, which activates particles around 3 nm.

Figure 18:
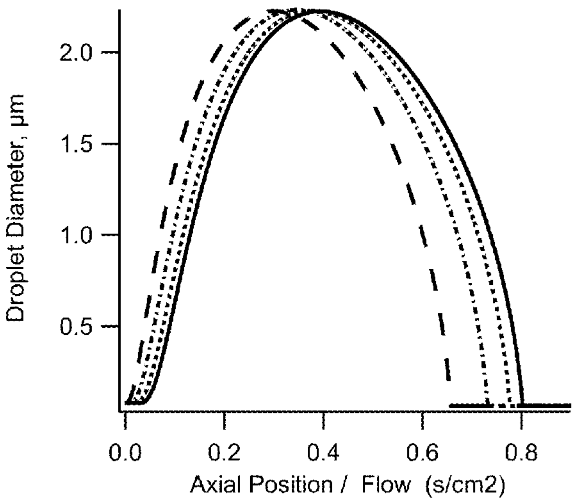
FIG. 18 shows the evolution of droplet size along four flow trajectories within the initiator-evaporator configuration.

FIG. 18 shows corresponding droplet growth for this configuration. The droplets grow rapidly, achieving their maximum diameter at an axial position where the saturation ratio along the particle trajectory drops below 1. They then start to evaporate. In the normal situation, where the walls are wet throughout the growth region the droplet size is largest near the walls, where the flow is slower and the particles have more time to growth. Here, the droplet size is quite uniform, nearly independent of radial position, as shown. This is because the warm dry walls start to evaporate those near the walls first, which counteracts the time for additional growth. These model results show that it is possible to provide droplets of a uniform maximum diameter, independent of the radial position. If the tube were terminated at 0.36 s/$cm^2$, the exiting droplets would be quite uniform in size. If extended longer, the droplets evaporate, but this could provide a means to deliver a uniform amount of reactive vapor species, or electrical charge from the surrounding gas that would then stay with the particle upon evaporation.

Figure 19:
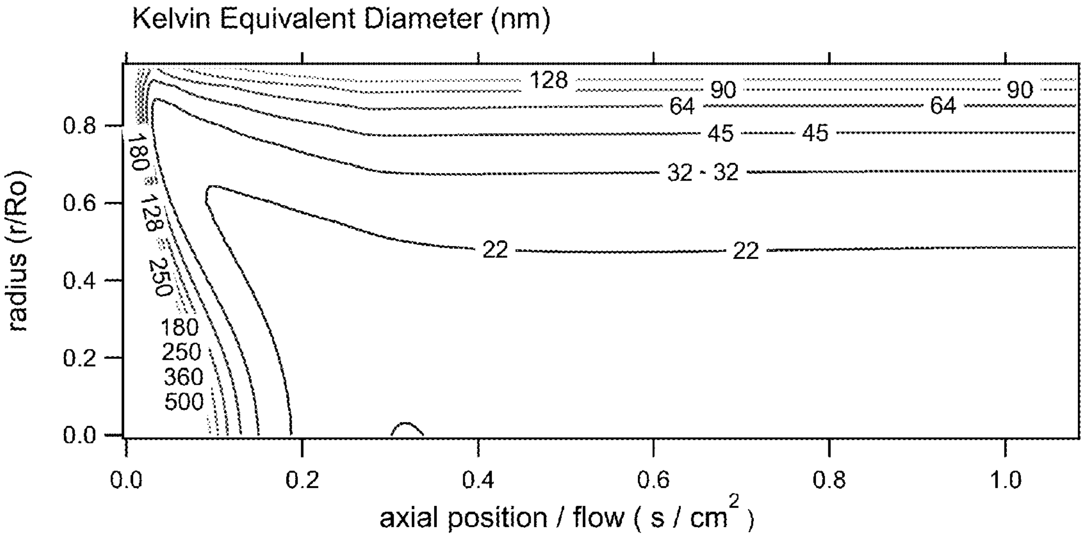
FIG. 19 shows the Kelvin equivalent diameter that results for an intitator-ramp configuration.

The fourth embodiment of the technology (FIG. 2*d* and FIG. 3*d*) once again uses an initiator, this time followed by a slow temperature ramp. Guided by the modeling it is possible to select an initial temperature jump at the initiator followed by temperature ramp that provides for uniform activation conditions along each particle trajectory. This is shown in FIG. 19, which plots the Kelvin equivalent diameter for the case of a tubular geometry at a volumetric flow rate of 1 L/min where the entering flow is 12° C., the initiator wall temperature is 25° C., followed by a 14 cm long ramp ending at 42° C. (or 1.2° C./cm). These profiles scale with the volumetric flow rate through the tube. With this configuration the Kelvin equivalent diameter is nearly constant along most of each flow trajectory. In all of the prior examples the saturation profile along a flow trajectory exhibits a strong maximum, and then decayed. By contrast, in this aspect of the technology, once the maximum Kelvin equivalent diameter is attained it is held for most of the rest of the flow trajectory. This provides a maximum time for activation and growth at low supersaturation ratio, as may be needed to activate hydrophobic particles. This specific approach was examined for the testing of diesel engine exhaust, where the required test protocol specifies detection of 50% of particles at 23 nm, and 90% or more at 40 nm.

Figure 20A:
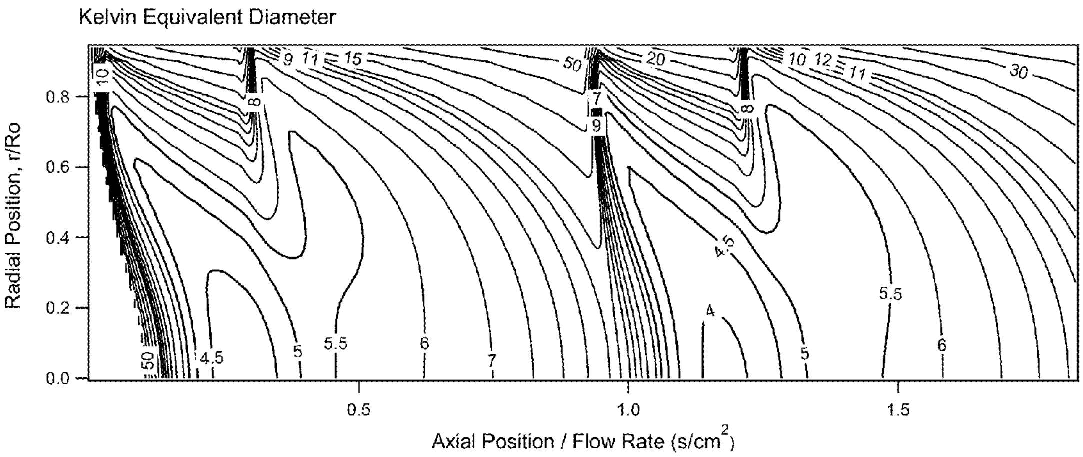
FIG. 20*a* shows Kelvin equivalent profiles and FIG. 20*b* the dew point for a four-stage condenser with two Initiator sections, each followed by an Equilibrator section.
Figure 20B:
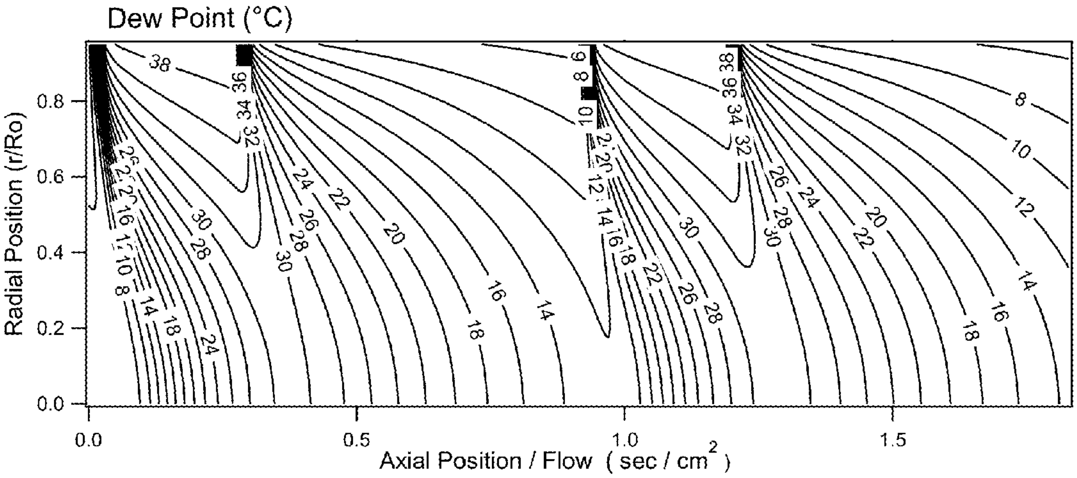
Figure 21A:
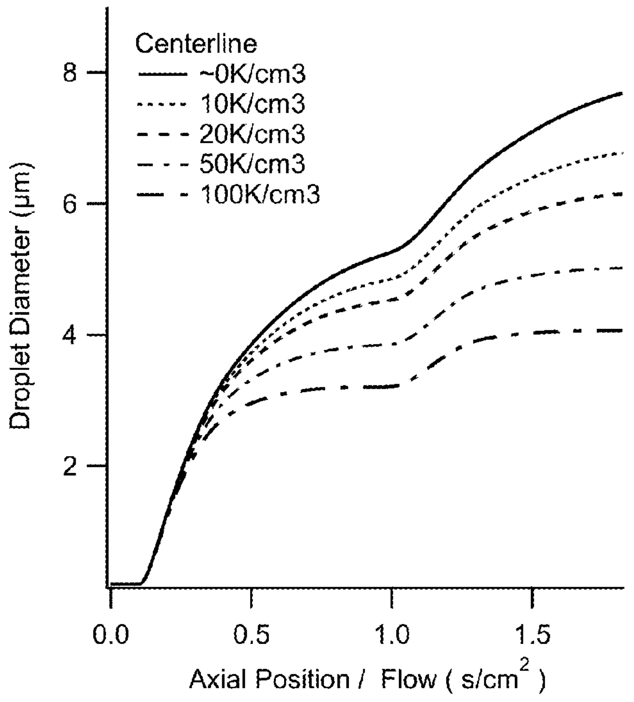
FIG. 21*a* shows the evolution of droplet size along the centerline and FIG. 21*b* shows the evolution of droplet size along the midpoint flow trajectories for the four-stage condenser of FIGS. 20*a* and 20*b*.
Figure 21B:
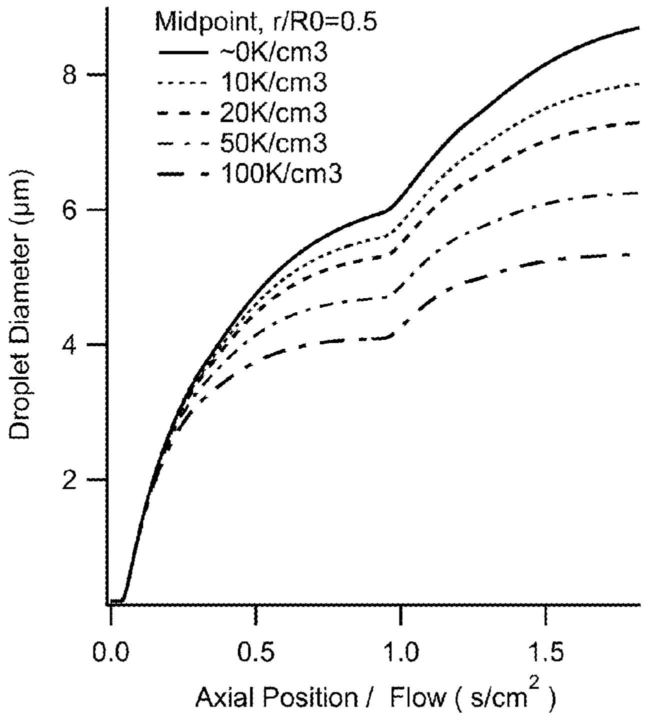

The aspects described above can also be combined to form a multistage condenser. For example, the Initiator-Equilibrator described in the second embodiment can be followed by another Initiator-Equilibrator. FIG. 20 shows the Kelvin equivalent diameter and dew point profiles for a four-stage condenser consisting of a 40° C. Initiator followed by a 5° C. Equilibrator, followed by a second 40° C. Initiator, followed by second 5° C. Equilibrator. The entering flow is at 5° C. and 95% RH, and the condenser walls are wetted throughout. The minimum Kelvin equivalent diameter and exiting dew point are not much changed from the simple two stage initiator-equilibrator configuration. However the droplets formed are much larger, especially for sampled concentrations below $5\times10^4$ $cm^{-3}$. The larger droplet size makes it easier to detect the droplets optically, or to collect them through inertial means.

In addition to the modeling presented above, droplet growth predictions have been experimentally validated for the first two embodiments of the technology described above. This was done using an aerodynamic particle sizer (Model 3021 available from TSI Inc., St. Paul, Minn.) to measure the exiting droplet diameters. For the single stage condenser, these laboratory measurements confirmed that reducing the diameter of the tube from 9.5 mm to 4.6 mm reduced the shift in droplet size with particle concentration. For the second embodiment, with the short initiator followed by the cold equilibrator, our experiments confirmed that this produced nearly the same droplet size as when operating with a single stage warm walled condenser of the same diameter and length. Moreover, rather than having rather restricted flow rate range over which the condenser was effective, with the two-stage initiator-equilibrator condenser it was possible to operate over a factor of 10 in flow rate. The maximum flow rate that produced a consistent droplet sizes corresponds to an initiator length to flow rate ratio of about 0.3 s/$cm^2$, in agreement with the modeling above. At lower flow rates the initiator was long compared to the position of maximum supersaturation, and the droplet growth was similar to that for a single stage condenser. The subsequent equilibrator simply served to provide a bit more time and distance for droplet growth while dropping the temperature and dew point.

All of the descriptions above apply to laminar flow condensers. However the equilibrator of the second embodiment of the technology could also be used as the second stage of a condenser where the first stage mixes two saturated flows at different temperatures. Mixing of saturated flows at differing temperatures is a well-established method for producing vapor supersaturation, and works with any type of condensing vapor, and is a result of the nonlinear nature of the vapor pressure equilibrium curve. Just as an equilibrator is used as the second stage of the laminar flow condenser to reduce the dew point and temperature while continuing the droplet growth, our models also show that such an equilibrator may be used as the second stage of a mixing type condenser, and similarly lowers the dew point without greatly affecting the relative humidity, and hence continues to promote the droplet growth.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for creating water vapor supersaturation in an airflow, comprising:

introducing an airstream in a laminar flow into a condenser at an inlet, the airstream having temperature of T1 at the inlet, the condenser having an outlet, the condenser having at least one wick providing wetted walls;

controlling a first portion of the condenser to a first temperature T2 greater than T1, the first portion having a first length and being adjacent to the inlet, and having wetted walls; and controlling a second portion of the condenser, the second portion having a second length longer than the first length and positioned between the first portion and the outlet and having wetted walls, the controlling providing provide a ramped temperature gradient along the second length of the second portion which increases from T2 to a temperature T3, the temperature T3 being greater than T2.

2. The method of claim 1 wherein said introducing comprises introducing the airstream into a preconditioner prior to said inlet, the airstream having a temperature T0 at an inlet to the preconditioner and the method further comprising controlling walls of the preconditioner to a temperature near T1.

3. The method of claim 1 wherein the condenser is cylindrical in shape.

4. The method of claim 1 wherein the condenser is comprised of several cylindrical tubes in parallel.

5. The method of claim 1 wherein the condenser is comprised of one or more parallel plates.

6. The method of claim 1 wherein T2 is about 10° C. to 20° C. greater than T1.

7. The method of claim 1 wherein controlling the second portion provides a rate of temperature increase in the second portion defined by a quantity (T3−T2)/L is in a range of about 1° C./cm to 2° C./cm.

8. The method of claim 1 wherein the step of introducing an airstream includes surrounding the airflow with a saturated airflow at temperature T2 higher than T1.

9. The method of claim 1 wherein the first portion and the second portion of the condenser define a volume, wherein intruding air into the condenser creates a volumetric air flow rate within the volume, and wherein a ratio of the first length of the first portion to the volumetric air flow rate is less than 0.3 s/cm2.

10. An apparatus comprising a condenser, the condenser formed by a container, comprising:

at least one wick providing wetted walls in the container;

an initiator comprising a first portion of the container and having wetted walls, the initiator having walls and configured to provide the walls at a temperature of T2, the temperature T2 greater than a temperature T1 of an incoming flow into the initiator; and a stabilizer coupled directly to a initiator and having wetted walls, the stabilizer having walls having a length between the initiator and an output of the stabilizer, the stabilizer configured to provide the walls of the stabilizer at an increasing temperature gradient between T2 and T3 along the length of the stabilizer to the output, where T3 is greater than T2.

11. The apparatus of claim 10 wherein the container is cylindrical in shape.

12. The apparatus of claim 10 wherein the container is comprised of several cylindrical tubes in parallel.

13. The apparatus of claim 10 wherein the container is comprised of one or more parallel plates.

14. The apparatus of claim 10 wherein T2 is about 10° C. to 20° C. greater than T1.

15. The apparatus of claim 10 wherein a rate of temperature increase in the stabilizer is defined by a quantity (T3−T2)/L is about 1° C./cm to 2° C./cm.

16. An apparatus creating water vapor supersaturation in an airflow, comprising:

a preconditioner having an input and an output, the input configured to receive an input airflow, and having walls between an input and an output and configured to maintain a temperature of T1; and a condenser having at lease tone wick providing wetted walls, a first portion coupled to the output of the preconditioner, the first portion having wetted walls and the condenser configured to provide the wetted walls of the first portion at a temperature T2, the temperature T2 greater than temperature T1;

the condenser having a second portion coupled to the first portion, the second portion having wetted walls having a length between the first portion and an output of the condenser, the second portion configured to provide the walls of the second portion at an increasing temperature gradient along the length of the second portion increasing between T2 and T3 to the output of the condenser, where T3 is greater than T2.

17. The apparatus of claim 16 wherein the first portion and the second portion of the condenser define a volume, wherein intruding air into the condenser creates a volumetric air flow rate within the volume, and wherein a ratio of a length of the first portion to the volumetric air flow rate is less than 0.3 s/cm2.

18. The apparatus of claim 16 wherein T2 is about 10° C. to 20° C. greater than T1.

19. The apparatus of claim 16 wherein a rate of temperature increase in the second portion of the condenser is defined by a quantity (T3−T2)/L is about 1° C./cm to 2° C./cm.

20. The apparatus of claim 16 wherein the preconditioner is configured to surround the airflow with a saturated airflow at temperature T2 higher than T1.

* * * * *

UNITED STATES PATENT AND TRADEMARK OFFICE
CERTIFICATE OF CORRECTION

PATENT NO. : 9,821,263 B2
APPLICATION NO. : 14/318126
DATED : November 21, 2017
INVENTOR(S) : Hering et al.

Page 1 of 1

It is certified that error appears in the above-identified patent and that said Letters Patent is hereby corrected as shown below:

In the Claims

Column 16, Line 45 (Claim 1, Line 11), please change "wetted" to -- water-wetted --.
Column 16, Line 49 (Claim 1, Line 15), please change "wetted" to -- water-wetted --.
Column 17, Line 16 (Claim 10, Line 3), please change "wetted" to -- water-wetted --.
Column 17, Line 18 (Claim 10, Line 5), please change "wetted" to -- water-wetted --.
Column 17, Line 23 (Claim 10, Line 10), please change "wetted" to -- water-wetted --.
Column 18, Line 7 (Claim 16, Line 7), please change "wetted" to -- water-wetted --.
Column 18, Line 9 (Claim 16, Line 9), please change "wetted" to -- water-wetted --.
Column 18, Line 14 (Claim 16, Line 14), please change "wetted" to -- water-wetted --.

Signed and Sealed this
Thirteenth Day of March, 2018

Andrei Iancu
*Director of the United States Patent and Trademark Office*